United States Patent
Aggarwal et al.

(10) Patent No.: US 10,729,727 B2
(45) Date of Patent: *Aug. 4, 2020

(54) MESENCHYMAL STEM CELLS AND USES THEREFOR

(71) Applicant: Mesoblast International Sárl, Meyrin (CH)

(72) Inventors: Sudeepta Aggarwal, North Potomac, MD (US); Mark F. Pittenger, Severna Park, MD (US); Timothy Varney, Baltimore, MD (US)

(73) Assignee: Mesoblast International Sárl, Meyrin (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/204,936

(22) Filed: Nov. 29, 2018

(65) Prior Publication Data

US 2019/0175657 A1   Jun. 13, 2019

Related U.S. Application Data

(63) Continuation of application No. 14/138,577, filed on Dec. 23, 2013, which is a continuation of application No. 13/222,778, filed on Aug. 31, 2011, now abandoned, which is a continuation of application No. 12/908,119, filed on Oct. 20, 2010, now abandoned, which is a continuation of application No. 11/541,853, filed on Oct. 2, 2006, now abandoned, which is a continuation-in-part of application No. 11/080,298, filed on Mar. 15, 2005, now abandoned.

(60) Provisional application No. 60/555,118, filed on Mar. 22, 2004.

(51) Int. Cl.
| | |
|---|---|
| *A61K 35/28* | (2015.01) |
| *C12N 5/0775* | (2010.01) |
| *A61K 38/20* | (2006.01) |
| *A61K 45/06* | (2006.01) |
| *A61K 35/12* | (2015.01) |

(52) U.S. Cl.
CPC .......... *A61K 35/28* (2013.01); *A61K 38/2026* (2013.01); *A61K 38/2066* (2013.01); *A61K 45/06* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *A61K 2035/124* (2013.01); *Y02A 50/409* (2018.01)

(58) Field of Classification Search
CPC .................................................... A61K 35/28
See application file for complete search history.

(56) References Cited

U.S. PATENT DOCUMENTS

| | | |
|---|---|---|
| 5,486,359 A | 1/1996 | Caplan I et al. |
| 5,700,691 A | 12/1997 | Bender et al. |
| 5,843,425 A | 12/1998 | Sachs et al. |
| 6,010,696 A | 1/2000 | Caplan I et al. |
| 6,077,987 A | 6/2000 | Breitbart et al. |
| 6,328,960 B1 | 12/2001 | McIntosh et al. |
| 6,355,239 B1 | 3/2002 | Bruder et al. |
| 6,497,875 B1 | 12/2002 | Sorrell et al. |
| 6,905,678 B2 * | 6/2005 | Havenga ................ C12N 15/86 424/93.2 |
| 8,940,293 B2 | 1/2015 | Li et al. |
| 9,694,035 B2 | 7/2017 | Aggarwal et al. |
| 9,943,547 B2 | 4/2018 | Aggarwal et al. |
| 2002/0037278 A1 | 3/2002 | Ueno et al. |
| 2002/0044923 A1 * | 4/2002 | Mosca ............. C07K 14/70521 424/93.21 |
| 2002/0045260 A1 | 4/2002 | Hung et al. |
| 2002/0064519 A1 | 5/2002 | Bruder et al. |
| 2002/0110544 A1 | 8/2002 | Goldberg et al. |
| 2003/0049843 A1 | 3/2003 | Havenga et al. |
| 2003/0059412 A1 | 3/2003 | Prockop et al. |
| 2003/0118567 A1 | 6/2003 | Stewart |
| 2003/0139410 A1 | 7/2003 | Sugaya et al. |
| 2004/0009155 A1 * | 1/2004 | Palasis ................. A61K 9/0019 424/93.21 |
| 2004/0018174 A1 | 1/2004 | Palasis |
| 2004/0022787 A1 * | 2/2004 | Cohen .............. C07K 14/70521 424/144.1 |
| 2004/0166097 A1 | 8/2004 | Prockop et al. |
| 2005/0093044 A1 | 5/2005 | Cheng et al. |
| 2005/0158397 A1 | 7/2005 | Chopp et al. |
| 2005/0239897 A1 | 10/2005 | Pittenger et al. |
| 2006/0112365 A1 | 5/2006 | Ito et al. |
| 2014/0154276 A1 | 6/2014 | Aggarwal et al. |
| 2014/0161776 A1 | 6/2014 | Aggarwal et al. |
| 2015/0272997 A1 | 10/2015 | Aggarwal et al. |

(Continued)

FOREIGN PATENT DOCUMENTS

| | | |
|---|---|---|
| CA | 2473108 A1 | 7/2003 |
| CN | 1382450 A | 12/2002 |

(Continued)

OTHER PUBLICATIONS

Davenport et al. (International Immunopharmacology. 2002; 2: 653-672) (Year: 2002).*

(Continued)

*Primary Examiner* — Scott Long

(74) *Attorney, Agent, or Firm* — Sterne, Kessler, Goldstein & Fox P.L.L.C.

(57) ABSTRACT

Compositions and methods of promoting wound healing in a human by administering to the human mesenchymal stem cells in an effective amount.

23 Claims, 9 Drawing Sheets

Specification includes a Sequence Listing.

(56) References Cited

U.S. PATENT DOCUMENTS

| | | |
|---|---|---|
| 2018/0291347 A1 | 10/2018 | Tom et al. |
| 2019/0175657 A1 | 6/2019 | Aggarwal et al. |
| 2019/0240259 A1 | 8/2019 | Aggarwal et al. |

FOREIGN PATENT DOCUMENTS

| | | |
|---|---|---|
| CN | 1536075 A | 10/2004 |
| EP | 1279738 A1 | 1/2003 |
| EP | 1391505 A1 | 2/2004 |
| JP | 198548933 | 4/1985 |
| JP | 1989501792 | 6/1989 |
| JP | 2003137898 A | 5/2003 |
| JP | 2003520254 A | 7/2003 |
| JP | 2004506598 A | 3/2004 |
| JP | 2004507454 A | 3/2004 |
| JP | 2004559434 | 3/2006 |
| JP | 2006510675 A | 3/2006 |
| JP | 4554940 B2 | 9/2010 |
| KR | 20040016785 A | 2/2004 |
| KR | 20040022134 A | 3/2004 |
| WO | WO-8705518 A1 | 9/1987 |
| WO | WO-9630031 A1 | 10/1996 |
| WO | WO-9741208 A1 | 11/1997 |
| WO | WO-9820731 A1 | 5/1998 |
| WO | WO-9943286 A2 | 9/1999 |
| WO | WO-9947163 A2 | 9/1999 |
| WO | WO-9951247 A1 | 10/1999 |
| WO | WO-9951275 A2 | 10/1999 |
| WO | WO-0006701 A1 | 2/2000 |
| WO | WO-0049136 A1 | 8/2000 |
| WO | WO-0053795 A1 | 9/2000 |
| WO | WO-0126470 A1 | 4/2001 |
| WO | WO-0152904 A2 | 7/2001 |
| WO | WO-0162901 A2 | 8/2001 |
| WO | WO-0132189 A1 | 10/2001 |
| WO | WO-0180865 A2 | 11/2001 |
| WO | WO-0208389 A2 | 1/2002 |
| WO | WO-02064182 A2 | 8/2002 |
| WO | WO-03003090 A1 | 1/2003 |
| WO | WO-03004661 A2 | 1/2003 |
| WO | WO-03010305 A1 | 2/2003 |
| WO | WO-03018077 A1 | 3/2003 |
| WO | WO-03020908 A2 | 3/2003 |
| WO | WO-03039489 A2 | 5/2003 |
| WO | WO-03059272 A2 | 7/2003 |
| WO | WO-03059276 A2 | 7/2003 |
| WO | WO-03068248 A1 | 8/2003 |
| WO | WO-03078567 A2 | 9/2003 |
| WO | WO-03078609 A1 | 9/2003 |
| WO | WO-03085099 A2 | 10/2003 |
| WO | WO-03105908 A2 | 12/2003 |
| WO | WO-2004003164 A2 | 1/2004 |
| WO | WO-2004006942 A1 | 1/2004 |
| WO | WO-2004007697 A2 | 1/2004 |
| WO | WO-2004011621 A2 | 2/2004 |
| WO | WO-2004022579 A2 | 3/2004 |
| WO | WO-2004052177 A2 | 6/2004 |
| WO | WO-2004084950 A2 | 10/2004 |
| WO | WO-2005001076 A2 | 1/2005 |
| WO | WO-2005013885 A2 | 2/2005 |
| WO | WO-2005093044 A1 | 10/2005 |
| WO | WO-2006112365 A1 | 10/2006 |
| WO | WO-2007084354 A2 | 7/2007 |
| WO | WO-2007124594 A1 | 11/2007 |
| WO | WO-2008042174 A2 | 4/2008 |
| WO | WO-2008116157 A2 | 9/2008 |

OTHER PUBLICATIONS

Loots et al. (J Invest Dermatol. 1998; 111: 850-857). (Year: 1998).*

Tateishi-Yuyama et al. (The Lancet. Aug. 10, 2002; 360(9331): 427-427). (Year: 2002).*

Aggarwal, S., et al., "Human Mesenchymal Stem Cells Modulate Allogeneic Immune Cell Responses," Blood 105(4):1815-1822, American Society of Hematology, United States (Feb. 2005).

Akiyama, Y., et al., "Remyelination of the Rat Spinal Cord by Transplantation of Identified Bone Marrow Stromal Cells," Journal of Neuroscience 22(15):6623-6630, Society for Neuroscience, United States (Aug. 2002).

Al-Khaldi, A., et al., "Postnatal Bone Marrow Stromal Cells Elicit A Potent VEGF-dependent Neoangiogenic Response In Vivo," Gene Therapy 10(8):621-629, Nature Publishing Group, England (Apr. 2003).

Al-Khaldi, A., et al., "Therapeutic Angiogenesis Using Autologous Bone Marrow Stromal Cells: Improved Blood Flow In a Chronic Limb Ischemia Model," Annals of Thoracic Surgery 75(1):204-209, Elsevier, Netherlands (Jan. 2003 ).

Andreef, Blood, 102(11), 60a, (2003).

Ballas, C.B., et al., "Adult Bone Marrow Stem Cells for Cell and Gene Therapies: Implications for Greater Use," Journal of Cellular Biochemistry 38:20-28, Liss, United States (2002).

Barry, F., et al., "The SH-3 and SH-4 Antibodies Recognize Distinct Epitopes on CD73 from Human Mesenchymal Stem Cells," Biochemical and Biophysical Research Communications 289(2):519-524, Elsevier, United States (Nov. 2001).

Barry, F.P., et al., "Biology And Clinical Applications of Mesenchymal Stem Cells," Birth Defects Research Part C: Embryo Today 69(3):250-256, Wiley Periodicals, Inc., United States (Aug. 2003).

Bartholomew, A., et al., "Mesenchymal Stem Cells Suppress Lymphocyte Proliferation In Vitro And Prolong Skin Graft Survival In Vivo," Experimental Hematology 30(1):42-48, Elsevier Science Inc., Netherlands (Jan. 2002).

Bell, R.G., "IgE, Allergies and Helminth Parasites: A New Perspective on an Old Conundrum," Immunology and Cell Biology 74(4):337-345, Nature Publishing Group, England (Aug. 1996).

Boucher, R.C, "New Concepts of the Pathogenesis of Cystic Fibrosis Lung Disease," The European Respiratory Journal 23(1):146-158, European Respiratory Society, England (Jan. 2004).

Bouma, G. & Strober, W., The immunological and genetic basis of inflammatory bowel disease, Nat. Rev. Immunol., 3, 521-533, Jul. 2003.

Bouma, G and Strober, W, "The Immunological and Genetic Basis of Inflammatory Bowel Disease," Nature Reviews, Immunology 3(7):521-533, Nature Publishing Group, England (Jul. 2003).

Brittan, M., et al., "Gastrointestinal Stem Cells," The Journal of Pathology 197(4):492-509, John Wiley And Sons, England (Jul. 2002 ).

Bruck, W., et al., "Remyelination in Multiple Sclerosis," Journal of the Neurological Sciences 206(2):181-185, Elsevier, Netherlands (Feb. 2003).

Bruder, S.P., et al., "The Effect of Implants Loaded With Autologous Mesenchymal Stem Cells on the Healing of Canine Segmental Bone Defects," The Journal of Bone and Joint Surgery. American 80(7):985-996, Journal of Bone and Joint Surgery, United States (Jul. 1998).

Burt, R.K., et al., "The Promise of Hematopoietic Stem Cell Transplantation for Autoimmune Diseases," Bone Marrow Transplant 31(7):521-524, Nature Publishing Group, England (Apr. 2003 ).

Carmeliet, P., et al., "The Emerging Role of the Bone Marrow-derived Stem Cells in (Therapeutic) Angiogenesis," Thrombosis and Haemostasis 86(1):289-297, Schattauer, Germany (Jul. 2001 ).

Chopp, M., et al., "Spinal Cord Injury In Rat: Treatment With Bone Marrow Stromal Cell Transplantation," NeuroReport 11(13):3001-3005, Lippincott Williams & Wilkins, England (Sep. 2000).

Chopp, M., et al., "Treatment of Neural Injury With Marrow Stromal Cells," The Lancet Neurology 1(2):92-100, Lancet Pub. Group, England (Jun. 2002).

Conese, M., et al., "Stem Cells and Cystic Fibrosis," Cystic Fibrosis 5(3):141-143, Elsevier, Netherlands (Aug. 2006).

Database WPI Week 200679, Thomson Scientific, London, GB; XP002545400, AN 2006-781676, & WO 2006/112365 A (Japan Health Sci Found), Sep. 17, 2009.

De Kok, I.J., et al., "Investigation of Allogeneic Mesenchymal Stem Cell-based Alveolar Bone Formation: Preliminary Findings," Clinical Oral Implants Research 14(4):481-489, John Wiley and Sons, Inc., Denmark (Aug. 2003).

(56) References Cited

OTHER PUBLICATIONS

De Miguel, M.P., et al., "Immunosuppressive Properties of Mesenchymal Stem Cells: Advances and Applications," Current Molecular Medicine 12(5):574-591, Bentham Science Publishers, Netherlands (Jun. 2012).
Deng, Y., et al., "Efficiency of Adenoviral Vector Mediated CTLA4Ig Gene Delivery Into Mesenchymal Stem Cells," Chinese Medical Journal 116(11):1649-1654, Chinese Medical Association, China (Nov. 2003).
Devine, S.M., et al., "Mesenchymal Stem Cells Distribute To a Wide Range of Tissues Following Systemic Infusion into Nonhuman Primates," Blood 101(8):2999-3001, American Society of Hematology, United States (Apr. 2003).
Devine, S.M., et al., "Mesenchymal Stem Cells: Stealth and Suppression," Cancer 7(2):S76S82, Lippincott Williams & Wilkins, United States (Nov.-Dec. 2001).
Di Nicola, M., et al., "Human Bone Marrow Stromal Cells Suppress T-Lymphocyte Proliferation Induced by Cellular or Nonspecific Mitogenic Stimuli," Blood 99(10):3838-3843, American Society of Hematology, United States (May 2002).
Djouad, F., et al., "Immunosuppressive Effect of Mesenchymal Stem Cells Favors Tumor Growth in Allogeneic Animals," Blood 102(10):3837-3844, American Society of Hematology, United States (Nov. 2003).
Dominici, M., et al., "Minimal Criteria for Defining Multipotent Mesenchymal Stromal Cells. The International Society for Cellular Therapy Position Statement," Cytotherapy 8(4):315-317, John Wiley and Sons, England (2006).
Durie, P.R., et al., "Characteristic Multiorgan Pathology of Cystic Fibrosis in a Long-living Cystic Fibrosis Transmembrane Regulator Knockout Murine Model," The American Journal of Pathology 164(4):1481-1493, Elsevier, United States (Apr. 2004).
Dzionek, A., et al., "BDCA-2, BDCA-3, and BDCA-4: Three Markers for Distinct Subsets of Dendritic Cells in Human Peripheral Blood," The Journal of Immunology 165(11):6037-6046, American Association of Immunologists, United States (Dec. 2000).
Eaves, C., et al., "Characterization of Human Hematopoietic Cells With Short-lived In Vivo Repopulating Activity," Annals of the New York Academy of Sciences 938:63-70, New York Academy of Sciences, United States (Jun. 2001).
El-Badri, N.S., et al., "Mesenchymal Stem Cells in Autoimmune Disease," Stem Cells and Development 13(5):463-472, Mary Ann Liebert, United States (Oct. 2004 ).
European Communication pursuant to Article 94(3) EPC in EP09009947.4-2107, dated May 21, 2010.
European Search Report for Application No. EP09009947, dated Sep. 23, 2009.
European Search Report for Application No. EP07861373, dated Mar. 2, 2009.
Extended European Search Report for Application No. EP10011226, dated Oct. 28, 2011.
Extended European Search Report for Application No. EP09009947, dated Sep. 11, 2009.
Extended European Search Report for Application No. EP10011223, dated Oct. 28, 2011.
Extended European Search Report for Application No. EP10011225, dated Mar. 11, 2011.
Extended European Search Report for European Application No. 16 171 424.1, dated Oct. 25, 2016.
Feng, "The Differentiation of Bone Marrow-derived Mesenchymal Stem Cells in Rat Lung and their Therapeutic Effects to Lung Injury," Chinese Excellent Ph.D. Thesis Database, Contribution for on-line publishing, Oct. 20, 2006.
Final Office Action dated Jan. 27, 2017, in U.S. Appl. No. 14/739,924, Aggarwal, S., et al., filed Jun. 15, 2015.
Frassoni et al 2002, Bone Marrow Transplant 29: S2,.
Frassoni, International Society for Cellular Therapy, SA006 (abstract) (2002).
Fukuda, K., "Development of Regenerative Cardiomyocytes From Mesenchymal Stem Cells for Cardiovascular Tissue Engineering," Artificial Organs 25(3):187-193, Wiley-Blackwell, United States (Mar. 2001).
Gao, J., et al., "The Dynamic in Vivo Distribution of Bone Marrow-derived Mesenchymal Stem Cells After Infusion," Cells, Tissues, Organs 169(1):12-20, Karger, Switzerland (2001).
Garcia-Olmo, D., et al., "Autologous Stem Cell Transplantation for Treatment of Rectovaginal Fistula in Perianal Crohn's Disease: A New Cell-based Therapy," International Journal of Colorectal Disease 18(5):451-454, Springer-Verlag, Germany (Sep. 2003).
Goncalves, M.A., "A Concise Peer Into the Background, Initial Thoughts and Practices of Human Gene Therapy ," BioEssays 27(5):506-517, Wiley, United States (May 2005).
Grom, A.A, "Natural Killer Cell Dysfunction: a Common Pathway in Systemic-onset Juvenile Rheumatoid Arthritis, Macrophage Activation Syndrome, and Hemophagocytic Lymphohistiocytosis?," Arthritis & Rheumatology 50(3):689-698, Wiley-Blackwell, United States (Mar. 2004).
Guan, X.Q., et al., "Study on Mesenchymal Stem Cells Entering the Brain Through the Blood-brain Barrier," Chinese Journal of Pediatrics 42(12):920-923, Chinese Medical Association, China (Dec. 2004).
Guo, Z., et al., "Biological Features of Mesenchymal Stem Cells From Human Bone Marrow," Chinese Medical Journal 114(9):950-953, Wolters Kluwer-Medknow, China (Sep. 2001).
Gupta, D., et al., "Adherence of Multiple Myeloma Cells to Bone Marrow Stromal Cells Upregulates Vascular Endothelial Growth Factor Secretion: Therapeutic Applications," Leukemia 15(12):1950-1961, Williams & Wilkins, England (Dec. 2001).
Hamada., H., et al., "Mesenchymal Stem Cells (MSC) as Therapeutic Cytoreagents for Gene Therapy," Cancer Science 96(3):149-156, Wiley Publishing, England (Mar. 2005).
Harris, S.G., et al., "Prostaglandins as Modulators of Immunity," Trends in Immunology 23(3):144-150, Elsevier Science Ltd., England (Mar. 2002).
Haynesworth, S.E., et al., "Characterization of Cells With Osteogenic Potential From Human Marrow," Bone 13(1):81-88, Elsevier Science, United States (1992).
Haynesworth, S.E., et al., "Cytokine Expression by Human Marrow-derived Mesenchymal Progenitor Cells in Vitro: Effects of Dexamethasone and IL-1 Alpha," Journal of Cellular Physiology 166(3):585-592, Wiley-Liss, United States (Mar. 1996).
Hori, Y., et al., "Experimental Study on Tissue Engineering of the Small Intestine by Mesenchymal Stem Cell Seeding," The Journal of Surgical Research 102(2):156-160, Academic Press, United States (Feb. 2002).
Horwitz, E.M., et al., "Clarification of the Nomenclature for MSC: The International Society for Cellular Therapy Position Statement," Cytotherapy 7(5):393-395, Elsevier, England (2005).
Horwitz, E.M., et al., "Clinical Responses to Bone Marrow Transplantation in Children With Severe Osteogenesis Imperfecta," Blood 97(5):1227-1231, American Society of Hematology, United States (Mar. 2001).
Horwitz, E.M., et al., "Isolated Allogeneic Bone Marrow-derived Mesenchymal Cells Engraft and Stimulate Growth in Children With Osteogenesis Imperfecta: Implications for Cell Therapy of Bone," Proceedings of the National Academy of Sciences of the United States of America 99(13):8932-8937, National Academy of Sciences, United States (Jun. 2002).
Ikehara, S., "Bone Marrow Transplantation: A New Strategy for Intractable Diseases," Drugs of Today 38(2):103-111, Clarivate Analytics, Spain (Feb. 2002).
Ikehara S., et al., "Treatment of Autoimmune Diseases by a New Bone Marrow Transplantation Method," Clinical and Experimental Medicine, 213(1), 96-98 (2005).
International Preliminary Report on Patentability for International Application No. PCT/US2007/20724, dated Apr. 16, 2009.
International Preliminary Report on Patentability for International Application No. PCT/US2008/57828, dated Oct. 1, 2009.
International Search Report and the Written Opinion for International Application No. PCT/US2007/20724, dated Apr. 17, 2008.

(56) References Cited

OTHER PUBLICATIONS

International Search Report and Written Opinion for International Application No. PCT/US2008/57828, European Patent Office, Rijswijk, dated Jan. 29, 2009, 15 pages.
International Search Report for International Application No. PCT/US2003/01129, dated Sep. 16, 2003.
International Search Report for International Application No. PCT/US2005/08506, dated Jul. 7, 2005.
International Search Report for International Application No. PCT/US2007/20724, dated Apr. 17, 2008.
Ishida, T., et al., "Requirement of Donor-derived Stromal Cells in the Bone Marrow for Successful Allogeneic Bone Marrow Transplantation. Complete prevention of Recurrence of Autoimmune Diseases in MRL/MP-lpr/lpr Mice by Transplantation of Bone Marrow plus Bones (Stromal Cells) From the Same Donor," The Journal of Immunology 152(6):3119-3127, American Association of Immunologists, United States (Mar. 1994).
Izadpanah, R., et al., "Biologic Properties of Mesenchymal Stem Cells Derived From Bone Marrow and Adipose Tissue," Journal of Cellular Biochemistry 99(5):1285-1297, Wiley-Liss, United States (Dec. 2006).
Japanese Office Action for Patent Application No. 2012-058539, dated Sep. 13, 2016.
Japanese Patent Office, Notice of reasons for rejection in Application No. 2014-124452, dated Jun. 19, 2015, 9 pages.
Jaquet, K., et al., "Reduction of Myocardial Scar Size After Implantation of Mesenchymal Stem Cells in Rats: What Is the Mechanism?," Stem Cells and Development 14(3):299-309, Mary Ann Liebert, Inc., United States (Jun. 2005).
Jones, J., et al., "Evaluation of Perianal Fistulas in Patients with Crohn's Disease," Medscape General Medicine 7(2):16, Medscape, United States (May 2005).
Jorgensen, C., et al., "Engineering Mesenchymal Stem Cells for Immunotherapy," Gene Therapy 10(10):928-931, Nature Publishing Group, England (2003).
Jorgensen, C., et al., "Mesenchymal Stem Cells and Rheumatoid Arthritis," Joint, Bone, Spine 70(6):483-485, Editions Elsevier, France (Dec. 2003).
Kassem, M., "Mesenchymal Stem Cells: Biological Characteristics and Potential Clinical Applications," Cloning and Stem Cells 6(4):369-374, Mary Ann Liebert, Inc., United States (2004).
King, T.E., et al., "Idiopathic Pulmonary Fibrosis: Relationship Between Histopathologic Features and Mortality," 164(6):1025-1032, American Thoracic Society, United States (Sep. 2001).
King, T.E, "Idiopathic Interstitial Pneumonias: Progress in Classification, Diagnosis, Pathogenesis and Management," Transactions of the American Clinical and Climatological Association 115:43-78, American Clinical and Climatological Association, United States (2004).
Kingsley, C.I., et al., "CD25+CD4+ Regulatory T Cells Prevent Graft Rejection: CTLA-4- and IL-10-dependent Immunoregulation of Alloresponses," Journal of Immunology 168(3):1080- 1086, American Association of Immunologists, United States (Feb. 2002).
Klyushnenkova., et al., "Human Mesenchymal Stem Cell-Mediated Suppression of Allogeneic T Cell Response: A Cytokine Analysis," FASEB, 13(4), A615, Mar. (1999).
Klyushnenkova., et al., "Human Mesenchymal Stem Cells Suppress Allogeneic T Cell Responses In Vitro: Implications for Allogen," Blood, 92(10), 642A, (Nov. 1998).
Koc, O.N., et al., "Allogeneic Mesenchymal Stem Cell Infusion for Treatment of Metachromatic Leukodystrophy (Mld) and Hurler Syndrome (MPS-IH)," Bone Marrow Transplant 30(4):215-222, Nature Publishing Group, England (Aug. 2002).
Koc, O.N., et al., "Rapid Hematopoietic Recovery After Coinfusion of Autologous-blood Stem Cells and Culture-expanded Marrow Mesenchymal Stem Cells in Advanced Breast Cancer Patients Receiving High-dose Chemotherapy," Journal of Clinical Oncology 18(2):307-316, American Society of Clinical Oncology, United States (Jan. 2000).
Kojima, R., et al., "Induction of Graft-versus-autoimmune (GVA) Disease Effect Against Refractory Psoriasis by Complete Donor-type Chimerism and Graft-versus-host Disease After Allogeneic Hematopoietic Stem Cell Transplantation," Bone Marrow Transplant 32(4):439-442, Nature Publishing Group, England (Aug. 2003).
Komori et al., 2005, Wound. Rep. Reg. 13:109-118.
Kotton, D.N., et al., "Bone Marrow-Derived Cells as Progenitors of Lung Alveolar Epithelium," Development 128(24):5181-5188, Company of Biologists Limited, England (2001).
Krampera, M., et al., "Bone Marrow Mesenchymal Stem Cells Inhibit the Response of Naive and Memory Antigen-specific T Cells to Their Cognate Peptide," Blood 101(9):3722-3729, American Society of Hematology, United States (May 2003).
Krause, D.S., et al., "Multi-organ, Multi-lineage Engraftment by a Single Bone Marrow-derived Stem Cell," Cell 105(3):369-377, Cell Press, United States (May 2001).
Krebsbach, P.H., et al., "Bone Marrow Stromal Cells: Characterization and Clinical Application," Critical Reviews in Oral Biology and Medicine 10(2):165-181, International Association for Dental Research, United States (1999).
Kushida, T., et al., "Crucial Role of Donor-derived Stromal Cells In Successful Treatment For Intractable Autoimmune Diseases In Mrl/Ipr Mice by Bmt Via Portal Vein," Stem Cells 19(3):226-235, AlphaMed Press, United States (2001).
Lazarus, H.M., et al., "Human Bone Marrow-derived Mesenchymal (Stromal) Progenitor Cells (Mpcs) Cannot Be Recovered From Peripheral Blood Progenitor Cell Collections," Journal of Hematotherapy 6(5):447-455, Mary Ann Liebert, Inc, United States (Oct. 1997).
Le Blanc, K. and Ringden, O., "Immunobiology of Human Mesenchymal Stem Cells and Future Use in Hematopoietic Stem Cell Transplantation," Biology of Blood and Marrow Transplantation 11(5):321-334, Carden Jennings Publishing, United States (May 2005).
Le Blanc, K., et al., "HLA Expression and Immunologic Properties of Differentiated and Undifferentiated Mesenchymal Stem Cells," Experimental Hematology 31(10):890-896, Elsevier Science Inc, Netherlands (Oct. 2003).
Le Blanc, K., et al., "Mesenchymal Stem Cells Inhibit and Stimulate Mixed Lymphocyte Cultures and Mitogenic Responses Independently of the Major Histocompatibility Complex," Scandinavian Journal of Immunology 57(1):11-20, Blackwell Scientific Publications, England (Jan. 2003).
Le Blanc, K., et al., "Treatment of Severe Acute Graft-Versus-Host Disease With Third Party Haploidentical Mesenchymal Stem Cells," Lancet 363(9419):1439-1441, Elsevier, England (May 2004).
Le Blanc, K., "Immunomodulatory Effects of Fetal and Adult Mesenchymal Stem Cells," Cytotherapy 5(6):485-489, Elsevier, England (2003).
Lee et al., "Treatment of high-risk acute myelogenous leukaemia by myeloblative chemoradiotherapy followed by co- nfusion ofT cell-depleted haematopoietic stem cells and culture-expanded marrow mesenchymal stem cells from elated donor with one fully mismatched human leucocyte antigen haplotype," British Journal of Haematology, pp. 1138-1131, 2002.
Lennon, D.P., et al., "Human and Animal Mesenchymal Progenitor Cells From Bone Marrow: Identification of Serum for Optimal Selection and Proliferation," In Vitro Cellular & Developmental Biology 32(10):602-611 (Nov. 1996).
Lopez-Cubero, S.O., et al., "Course of Crohn's Disease After Allogeneic Marrow Transplantation," Gastroenterology 114(3):433-440, W.b. Saunders, United States (Mar. 1998).
Ltoyama Y., et al., "New Immunotherapy for Multiple Sclerosis," Shinkei-Chiryo (Neurological Therapeutics), 15(4), 355-358, (1998).
Maassen, C.B., et al., "Reduced Experimental Autoimmune Encephalomyelitis After Intranasal and Oral Administration of Recombinant Lactobacilli Expressing Myelin Antigens," Vaccine 21(32):4685-4693, Elsevier Science, Netherlands (Dec. 2003).
Mackenzie, T.C. and Flake, A.W., "Human Mesenchymal Stem Cells Persist, Demonstrate Site-specific Multipotential Differentiation, and Are Present in Sites of Wound Healing and Tissue

(56) References Cited

OTHER PUBLICATIONS

Regeneration After Transplantation Into Fetal Sheep," Blood Cells, Molecules & Diseases 27(3):601-604, Academic Press, United States (May 2001).

Maitra, B., et al., "Human Mesenchymal Stem Cells Support Unrelated Donor Hematopoietic Stem Cells and Suppress T-cell Activation," Bone Marrow Transplant 33(6):597-604, Nature Publishing Group, England (Mar. 2004).

Majumdar, M.K., et al., "Characterization and Functionality of Cell Surface Molecules on Human Mesenchymal Stem Cells," Journal of Biomedical Science 10(2):228-241, BioMed Central, England (Mar.-Apr. 2003).

Majumdar, M.K., et al., "Human Marrow-derived Mesenchymal Stem Cells (MSCs) Express Hematopoietic Cytokines and Support Long-term Hematopoiesis When Differentiated Toward Stromal and Osteogenic Lineages," Journal of Hematotherapy & Stem Cell Research 9(6):841848, Mary Ann Liebert, Inc., United States (Dec. 2000).

Mangi, A.A., et al., "Mesenchymal Stem Cells Modified With Akt Prevent Remodeling and Restore Performance of Infarcted Hearts," Nature Medicine 9(9):1195-1201, Nature Publishing Company, United States (Sep. 2003).

Mansilla, E., et al., "Human Mesenchymal Stem Cells Are Tolerized by Mice and Improve Skin and Spinal Cord Injuries," Transplantation Proceedings 37(1):292-294, Elsevier Science Inc., United States (Jan.-Feb. 2005).

Matsui T., et al., "Kokomadekita Enshousei Choshikkan no Chiryou: Enshousei Shikkan no Yakubutu Ryouhou," Geka-chiryou, 89(3), 263-270, (Sep. 2003).

Matsuura, M., et al., "Effect of FTY720, A Novel Immunosuppressant, on Adjuvant-induced Arthritis in Rats," Inflammation Research 49(8):404-410, Birkhäuser, Switzerland (Aug. 2000).

McCombs, M.I, "Research in Cystic Fibrosis: a Review," Texas Reports on Biology and Medicine 31(4):615-629, University of Texas, United States (1973).

Meisel, R., et al., "Human Bone Marrow Stromal Cells Inhibit Allogeneic T-cell Responses by Indoleamine 2,3-Dioxygenase-Mediated Tryptophan Degradation," Blood 103(12):4619-4621, American Society of Hematology, United States (Jun. 2004 ).

Melgar, S., et al., "Over-expression of Interleukin 10 in Mucosal T Cells of Patients With Active Ulcerative Colitis," Clinical and Experimental Immunology 134(1):127-137, Blackwell Scientific Publications, England (Oct. 2003).

Merck Manual, 17th ed., Japanese version, published Dec. 10, 1999, pp. 305 and 308.

Minguell, J.J., et al., "Mesenchymal Stem Cells," Experimental Biology and Medicine 226(6):507-520, The Society, England (2001).

Miyahara, Y., et al., "Monolayered Mesenchymal Stem Cells Repair Scarred Myocardium After Myocardial Infarction," Nature Medicine 12(4):459-465, Nature Publishing Company, United States (Apr. 2006).

Moutsatsos, I.K., et al., "Exogenously Regulated Stem Cell-mediated Gene Therapy for Bone Regeneration," Molecular Therapy 3(4):449-461, Cell Press, United States (Apr. 2001).

Muraro, P.A., et al., "Using Stem Cells in Multiple Sclerosis Therapies," Cytotherapy 6(6):615-620, Elsevier, England (2004).

Naoki, "Present State of the Development of Therapeutic Agents of Multiple Sclerosis," Folia Pharmacologica Japonica, 117, 150-151, (2001).

Neuringer I.P., et al., "Stem Cells and Repair of Lung Injuries," Respiratory Research, 5, 6, (Jul. 2004).

Noel, D., et al., "Regenerative Medicine Through Mesenchymal Stem Cells for Bone and Cartilage Repair," Current Opinion in Investigational Drugs 3(7):1000-1004, Thomson Reuters, England (Jul. 2002).

Notice of Opposition against European Application No. 10011225.9, 26 pages, 2016.

Notice of Preliminary Rejection for Korean Application No. KR10-2015-7002664, dated Feb. 23, 2016.

Office Action for Japanese Patent App_ No. 2012-58539, dated Feb. 18, 2016.

Office Action in EP Application No. 10 011 224.2 dated Aug. 22, 2016.

Office Action dated Dec. 14, 2017, in U.S. Appl. No. 14/739,924, Aggarwal, S. et al., filed Jun. 15, 2015.

Office Action dated Jul. 12, 2016, in U.S. Appl. No. 14/739,924, Aggarwal, S. et al., filed Jun. 15, 2015.

Zhang, X., et al., "IL-10 is involved in the suppression of experimental autoimmune encephalomyelitis by CD25+CD4+ regulatory t cells," International Journal of Immunology 16(2):249-256, Japanese Society for Immunology, Japan (2004).

Office Action dated Nov. 25, 2015, in U.S. Appl. No. 14/739,924, Aggarwal, S. etal., filed Jun. 15, 2015.

Office Action dated Sep. 7, 2018, in U.S. Appl. No. 14/739,924, Aggarwal, S. et al., filed Jun. 15, 2015.

Ohlsson, L.B., et al., "Mesenchymal Progenitor Cell-mediated Inhibition of Tumor Growth in Vivo and in Vitro in Gelatin Matrix," Experimental and Molecular Pathology 75(3):248-255, Elsevier, Netherlands (Dec. 2003).

Okamoto, R., et al., "Damaged Epithelia Regenerated by Bone Marrow-derived Cells in the Human Gastrointestinal Tract," Nature Medicine 8(9):1011-1017, Nature Publishing Company, United States (Sep. 2002).

Ortiz, L.A., et al., "Mesenchymal Stem Cell Engraftment in Lung Is Enhanced in Response to Bleomycin Exposure and Ameliorates Its Fibrotic Effects," Proceedings of the National Academy of Sciences of the United States of America 100(14):8407-8411, National Academy of Sciences, United States (Jul. 2003).

Osamu Date, et al., "Investigation of the expansion of bone marrow mesenchymal stem cells in a mouse model of hind limb ischemia and angiogenesis by the transplantation of the cells," Japanese Journal of Cardiovascular Surgery, Japan, issued on Jan. 26, 2004, vol. 33, Supplement, 285.

Osamu Date, et al., "Study on revascularization by bone marrow Mesenchymal stem cells," Angiology, Japan, issued Sep. 25, 2003, vol. 43, No. 9, p. 557.

Oswald, J., et al., "Mesenchymal Stem Cells Can Be Differentiated Into Endothelial Cells in Vitro," Stem Cells 22(3):377-384, AlphaMed Press, United States (2004).

Penn, M.S., "Stem Cells and Myocardial Regeneration," Humana Press Inc, 2010.

Pereira, R.F., et al., "Marrow Stromal Cells as a Source of Progenitor Cells for Nonhematopoietic Tissues in Transgenic Mice With a Phenotype of Osteogenesis Imperfecta," Proceedings of the National Academy of Sciences of the United States of America 95(3):1142-1147, National Academy of Sciences, United States (Feb. 1998).

Pichler, L., et al., "Preclinical Investigation of Alpha 1-acid Glycoprotein (Orosomucoid)," Wiener Klinische Wochenschrift 111(5):192-198, Springer, Austria (Mar. 1999).

Pittenger, M.F., et al., "Multilineage Potential of Adult Human Mesenchymal Stem Cells," Science 284(5411):143-147, American Association for the Advancement of Science, United States (Apr. 1999).

Potian, J.A., et al., "Veto-like Activity of Mesenchymal Stem Cells: Functional Discrimination Between Cellular Responses to Alloantigens and Recall Antigens," Journal of Immunology 171(7):3426-3434, American Association of Immunologists, United States (Oct. 2003).

Prockop, D.J., "Marrow Stromal Cells as Stem Cells for Nonhematopoietic Tissues," Science 276(5309):71-74, American Association for the Advancement of Science, United States (Apr. 1997).

Radice, M., et al., "Hyaluronan-based Biopolymers as Delivery Vehicles for Bone-marrow-derived Mesenchymal Progenitors," Journal of Biomedical Materials Research 50(2):101-109, Wiley, United States (May 2000).

Rasmusson, I., et al., "Mesenchymal Stem Cells Inhibit the Formation of Cytotoxic T Lymphocytes, but Not Activated Cytotoxic T Lymphocytes or Natural Killer Cells," Transplantation 76(8):1208-1213, Lippincott Williams & Wilkins, United States (Oct. 2003).

(56) References Cited

OTHER PUBLICATIONS

Reading, K., et al., "Peripheral Blood as an Alternative Source of Mesenchymal Stem Cells," Abstracts from the Eighth Workshop on Cell Biology of Bone and Cartilage in Health and Disease, Switzerland (2000).
Reyes, C.M.V., "Endothelial Cells Generated From Human Marrow Derived Mesenchymal Stem Cells (MSC)," Blood 96(11):530A, American Society of Hematology, United States (2000).
Ricardo, S.D. and Deane, J.A., "Adult Stem Cells in Renal Injury and Repair," Nephrology 10(3):276-282, Blackwell Science, Australia (Jun. 2005).
Rojas, M., et al., "Bone Marrow-derived Mesenchymal Stem Cells in Repair of the Injured Lung," American Journal of Respiratory Cell and Molecular Biology 33(2):145-152, American Thoracic Society, United States (Aug. 2005).
Saijo Y., et al., "Oncogene Therapy Using Mesenchymal Stem Cells," Respiratory Molecular Medicine, 8(5), 34-38, (2004).
Sakaida, I., et al., "Development of Cell Therapy Using Autologous Bone Marrow Cells for Liver Cirrhosis," Medical Molecular Morphology 38(4):197-202, Springer, Japan (Dec. 2005).
Sanchez-Ramos, J.R., et al., "Expression of Neural Markers in Human Umbilical Cord Blood," Experimental Neurology 171(1):109-115, Academic Press, United States (Sep. 2001).
Saunders Company, "Pathologic Basis of Disease," 9 pages, 1982.
Schwarz, E.J., et al., "Multipotential Marrow Stromal Cells Transduced to Produce L-DOPA: Engraftment in a Rat Model of Parkinson Disease," Human Gene Therapy 10(15):2539-2549, Liebert, United States (Oct. 1999).
Science Magazine, Multilineage Potential of Adult Human Mesenchymal Stem Cells, 1999, Retrieved from the Internet::< http://www.sciencemag.org/feature/data/983855.dtl>.
Selman, M., et al., "Idiopathic Pulmonary Fibrosis: Pathogenesis and Therapeutic Approaches," Drugs 64(4):405-430, Springer International, New Zealand (2004).
Semont, A., et al., "Mesenchymal Stem Cells Increase Self-Renewal of Small Intestinal Epithelium and Accelerate Structural Recovery after Radiation Injury," Advances in Experimental Medicine and Biology 585:19-30, Kluwer Academic/Plenum Publishers, United States (2006).
Shake, J.G., et al., "Mesenchymal Stem Cell Implantation in a Swine Myocardial Infarct Model: Engraftment and Functional Effects," The Annals of Thoracic Surgery 73(6):1919-1925, Elsevier, Netherlands (Jun. 2002).
Shin-Ichi., et al., "Feature Articles: Off-Label Drug Use in the Treatment of Neurologic Diseases: Immunoglobulins, Immunosuppressive Agents, Dehydroepiandrosterone Sulfate, and Corticosteroids," Shinkei-Chiryo (Neurological Therapeutics), 16(3), 351-359, (1999).
Shinomiya K., et al., "Shouni Zenshinsei Erimatodesu," Shouni Rinshou, 51(4), 204-208, (1998).
Shinomiya K., et al., "Systemic Lupus Erythematosus in Children," Sho-ni Rinsho (Clinical Pediatrics), 51, 404-410, (1998).
Shumakov, V.I., et al., "Mesenchymal Bone Marrow Stem Cells More Effectively Stimulate Regeneration of Deep Burn Wounds Than Embryonic Fibroblasts," Bulletin of Experimental Biology and Medicine 136(2):192-195, Springer, United States (Aug. 2003).
Snowden, J.A., et al., "Long-term Outcome of Autoimmune Disease Following Allogeneic Bone Marrow Transplantation," Arthritis and Rheumatism 41(3):453-459, Wiley-Blackwell, United States (Mar. 1998).
Ditschkowski, M., et al., "Improvement of Inflammatory Bowel Disease After Allogeneic Stem-cell Transplantation," Transplantation 75(10):1745-1747, Lippincott Williams & Wilkins, United States (May 2003).
Summons to attend oral proceedings pursuant to Rule 115(1) EPC for EP Application No. 07861373.4-1222, dated Feb. 4, 2010.
Supplementary European Search Report for EP Application No. EP05725577, European Patent Office, Munich, Germany, dated Jul. 10, 2007, 11 pages.

Tang, Y.L., et al., "Autologous Mesenchymal Stem Cell Transplantation Induce VEGF and Neovascularization in Ischemic Myocardium," Regulatory Peptides 117(1):3-10, Elsevier/North Holland, Netherlands (Jan. 2004).
Thannickal, V.J., et al., "Mechanisms of Pulmonary Fibrosis," Annual Review of Medicine 55:395-417, Annual Reviews, United States (2004).
Toma, C., et al., "Human Mesenchymal Stem Cells Differentiate to a Cardiomyocyte Phenotype in the Adult Murine Heart," Circulation 105(1):93-98, Lippincott Williams & Wilkins, United States (Jan. 2002).
Tomita, S., et al., "Autologous Transplantation of Bone Marrow Cells Improves Damaged Heart Function," Circulation 100(19):11247-11256, Lippincott Williams & Wilkins, United States (Nov. 1999).
Tondreau, T., et al., "The Potential of Human Bone Marrow-derived Mesenchymal Stem Cells to Differentiate in Neural Cells," Blood 98(11):125b, American Society of Hematology, United States (2001).
Tse, W.T., et al., "Suppression of Allogeneic T-cell Proliferation by Human Marrow Stromal Cells: Implications in Transplantation," Transplantation 75(3):389-397, Lippincott Williams & Wilkins, United States (Feb. 2003).
Umezawa Y., et al., "Kanzen no Meneki Yokuseiyaku Chiryou niokderu Yakubutudoutai ni Motozuita Chiryouhou no Kakuritu," Kyou no Ishoku, 16, 609-611, (2003).
Van Laar, J.M., et al., "Adult Stem Cells in the Treatment of Autoimmune Diseases," Rheumatology (Oxford) 45(10):1187-1193, Oxford University Press, England (Oct. 2006; online Jun. 15, 2016).
Vassiliou, E., et al., "Prostaglandin E2 Inhibits TNF Production in Murine Bone Marrow-derived Dendritic Cells," Cellular Immunology 223(2):120-132, Elsevier, Netherlands (Jun. 2003).
Wagers, A.J., et al., "Cell Fate Determination From Stem Cells," Gene Therapy 9(10):606612, Nature Publishing Group, England (May 2002).
Wakitani, S., et al., "Myogenic Cells Derived From Rat Bone Marrow Mesenchymal Stem Cells Exposed to 5-azacytidine," Muscle & Nerve 18(12):1417-1426, John Wiley & Sons, United States (Dec. 1995).
Wang, G., et al., "Adult Stem Cells From Bone Marrow Stroma Differentiate Into Airway Epithelial Cells: Potential Therapy for Cystic Fibrosis," Proceedings of the National Academy of Sciences of the United States of America 102(1):186-191, National Academy of Sciences, United States (Jan. 2005).
Woodbury, D., et al., "Adult Bone Marrow Stromal Stem Cells Express Germline, Ectodermal, Endodermal, and Mesodermal Genes Prior to Neurogenesis," Journal of Neuroscience Research 69(6):908-917, Wiley Interscience, United States (Sep. 2002).
Wu, G.D., et al., "Migration of Mesenchymal Stem Cells to Heart Allografts During Chronic Rejection," Transplantation 75(5):679-685, Lippincott Williams & Wilkins, United States (Mar. 2003).
Wu, S., et al., "Bone Marrow Stromal Cells Enhance Differentiation of Cocultured Neurosphere Cells and Promote Regeneration of Injured Spinal Cord," Journal of Neuroscience Research 72(3):343-351, Wiley Interscience, United States (May 2003).
Young, R.G., et al., "Use of Mesenchymal Stem Cells in a Collagen Matrix for Achilles Tendon Repair," Journal of Orthopaedic Research 16(4):406-413, Raven Press, United States (Jul. 1998).
Ziobro, R., et al., "Ceramide Mediates Lung Fibrosis in Cystic Fibrosis," Biochemical and Biophysical Research Communications 434(4):705-709, Elsevier, United States (May 2013).
Zvaifler, N.J., et al., "Mesenchymal Precursor Cells in the Blood of Normal Individuals," Arthritis Research 2(6):477-488, Biomed Central Ltd, England (2000).
Final Office Action dated Feb. 2, 2016, in U.S. Appl. No. 14/138,577, Aggarwal, S., et al., filed Dec. 23, 2013.
Final Office Action dated Nov. 13, 2017, in U.S. Appl. No. 14/138,577, Aggarwal, S., et al., filed Dec. 23, 2013.
Non-Final Office Action dated Apr. 2, 2015, in U.S. Appl. No. 14/138,577, Aggarwal, S., et al., filed Dec. 23, 2013.
Non-Final Office Action dated Apr. 17, 2017, in U.S. Appl. No. 14/138,577, Aggarwal, S., et al., filed Dec. 23, 2013.
Non-Final Office Action dated Oct. 9, 2018, in U.S. Appl. No. 14/138,577, Aggarwal, S., et al., filed Dec. 23, 2013.

(56) References Cited

OTHER PUBLICATIONS

Al, G., et al., "The experimental study of bone marrow mesenchymal stem cells on the repair of skin wound combined with local radiation injury," Nat Med J. China 82(23):1632-1637, JAMA, China (2002).
Andrew, J.G., et al., "Inflammatory cells in normal human fracture healing," ACTA orth Scan 64(3):462-466, Taylor & Francis, United States (1994).
Bacigalupo, A., et al., "Management of acute graft versus host disease (GvHD)," Hematology Journal (5):189-196, The European Hematology Association (2004).
Badiavas, E.V., et al., "Treatment of chronic wounds with bone marrow-derived cells," Arch Dermatol 139(4):510-516, JAMA Dermatology, United States (2003).
Deans, R.J., et al., "Mesenchymal stem cells: biology and potential clinical uses," Exp Hematol 28(8):875-884, Elsevier, Netherlands (2000).
Gillitzer, R., et al., "Chemokines in cutaneous wound healing," J. Leukoc Biol 69(4):513-521, Wiley Online Library, United States (2001).
Heshmati, F., "Mechanisms of action of extracorporeal photochemotherapy," Transfusion and Apheresis Science 29(1):61-70, Elsevier, Netherlands (2003).
Lorimore, S.A, et al., "Inflammatory-type responses after exposure to ionizing radiation in vivo: a mechanism for radiation-induced bystander effects?," Oncogene 20(48):7085-7095, Nature Publishing Group, Britain (2001).
Lundberg, J.E., et al., "Comparison of IL-10 levels in chronic venous insufficiency ulcers and autologous donor tissue," Archives of Dermatological Research 290(12):669-673, Springer Link, United States (1998).
Phillips, S., "Physiology of Wound Healing and Surgical Wound Care," ASAIO Journal; S2-S5, National Institutes of Health, United States (2000).
Rasmusson, I., "Immune Modulation by mesenchymal stem cells," Exp Cell Res 312:2169-2179, Elsevier, Netherlands (2006).
Serhan, C.N., et al., "Resolution of Inflammation: state of the art, definitions and terms," FASEB J 21(2):325-332, FASEB, United States (2007).
Stedman's Medical Dictionary, 2ed Edition, pp. 1865, 1990., Lippincott Williams & Wilkins, Baltimore, United States (2000).
Wang, J.F., et al., "The Pig as a Model for Excisional Skin Wound Healing: Characterization of the Molecular and Cellular Biology, and Bacteriology of the Healing Process," Comparative Medicine 51(4): 341-348, American Association for Laboratory Animal Science, United Sates (2001).
Werner, S., et al., "Regulation of Wound Healing by Growth Factors and Cytokines," Physiol Rev 83:835-870, American Physiological Society, United States (2003).
Mast, B., et al., "Interaction of cytokines, growth factors, and proteases in acute and chronic wounds, " Wound Repair and Regeneration 4(4):411-420, OVID, Germany (1996).
Schultz, G., et al., "Wound bed preparation: a systematic approach to wound management, " Wound Repair and Regeneration 11(1):1-28, OVID, Germany (2003).
Collier, M., et al., "Understanding wound inflammation," Nursing Times 99(25):63, Jun. 24, 2003.
Zhao, R., et al., "Inflammation in Chronic Wounds," International Journal of Molecular Sciences 17:2085, MDPI, Switzerland (2016).
Lee., D., et al., "Mesenchymal stem cells and cutaneous wound healing: novel methods to increase cell delivery and therapeutic efficacy," Stem Cell Research & Therapy 7(37): 8 pages, Springer, United States (2016).
Gartner, S., et al., "Long-term culture of human bone marrow cells," Proc. Natl. Acad. Sci 77(8):4756-4759, United States national Academy of Sciences, United States (1980).
Dexter, T.M., et al., "Conditions Controlling the Proliferation of Hemopoietic Stem Cells in Vitro," J. Cell Physiol 91:335-334, Wiley-Liss, United States (1976).
Borzone, G., et al., "Bleomycin-Induced Chronic Lung Damage does not resemble human idiopathic Pulmonary Fibrosis," AM J Respir. Crit. Care Med 163:1648-1653, American Journal of Respiratory and Critical Care, United States (2001).
Kingwell, K., et al., " InterMune and Boehringer blaze trails for idiopathic pulmonary fibrosis drugs," Nature Reviews 13:483-484, Macmillan Publishers, United States (2014).
Song, E., et al., "Influence of Alternatively and Classical Activated Macrophages on Fibrogenic Activities of Human Fibroblasts," Cellular Immunology 204:19-28, Elsevier, United States (2000).
Maxson, S., et al., "Concise review: role of mesenchymal stem cells in wound repair," Stem Cells Translational Medicine 1:142-149, Wiley Online Library, United States (2012).
Sanjari, T., et al., "The Role of Mesenchymal Stem Cells in Skin Wound Healing," Journal of Cell and Molecular Research 7(2):70-77, Halic University, Turkey (2015).
Rapala, K., "The effect of Tumor Necrosis Factor-$\alpha$ on wound healing: an experimental study," Annales Chirurgiae et gynaecologiae, Finland, (1996).
Co-pending U.S. Appl. No. 16/206,235, inventors Aggarwal, S., et al., filed Nov. 30, 2018 (Not Published).
Co-pending U.S. Appl. No. 16/214,485, inventors Aggarwal, S., et al., filed Nov. 30, 2018 (Not Published).
Afzali, B., et al., "The Role of T helper 17 (Th17) and regulatory T cells (Treg) in human organ transplantation and autoimmune disease," Clinical and Experimental Immunology 148:32-46, British Society for Immunology, United Kingdom (2007).
Alho, H.S., et al., "Tumor Necrosis Factor-$\alpha$ in a Porcine Bronchial Model of Obliterative Bronchiolitis," Transplantation 76(3):516-523, Lippincott Williams * Wilkins, Inc., United States (2003).
Asanuma, H., et al., "Arterially Delivered Mesenchymal Stem Cells Prevent Obstruction-Induced Renal Fibrosis," Journal of Surgical Research 168(1):e51-e59, Elsevier, Netherlands (2011).
Baecher-Allan, C., et al., "$CD4^+CD25^{High}$ Regulatory Cells in Human Peripheral Blood," J. Immunol. 167:1245-1253, American Association of Immunologists, United States (2001).
Bai, L., et al., "Human Bone Marrow-Derived Mesenchymal Stem Cells induce TH2-Polarized Immune Response and Promote Endogenous Repair in Animal Models of Multiple Sclerosis," GLIA 57:1192-1203, Wiley Interscience, United States (2009).
Border, W.A., et al., "Transforming Growth Factor $\beta$ in Tissue Fibrosis," The New England Journal of Medicine 331(19):1286-1292, Massachusetts Medical Society, United States (1994).
Bowden, D.H., et al., "Unraveling Pulmonary Fibrosis: the Bleomycin Model," Laboratory Investigation 50(5):487, United States-Canadian Division of the International Academy of Pathology, United States (1984).
Brass, D.M., et al., "Reduced Tumor Necrosis Factor-$\alpha$ and transforming Growth Factor-$\beta$1 Expression in the Lungs of Inbred Mice that Fail to Develop Fibroproliferative Lesions Consequent to Asbestos Exposure," American Journal of Pathology 154(3):853-862, American Society for Investigative Pathology, United States (1999).
Ciccocioppo, R., et al., "Autologous bone marrow-derived mesenchymal stromal cells in the treatment of fistulising Crohn's disease," Gut: 11 pp., Biomedical Journal, Denmark (2011).
Coppo, R., et al., "New Perspectives in treatment of glomerulonephritis," Pediatr Nephrol 19:256-265, Springer, United States (2004).
Duijvestein, M., et al., "Autologus bone marrow-derived mesenchymal stromal cell treatment for refractory luminal Crohn's disease: results of a phase I study," GUT: 1662-1669, Biomedical Journal, Denmark (2010).
Distler, J.H.W., et al., "The Controversial Role of Tumor Necrosis Factor $\alpha$ in Fibrotic Diseases," Arthritis & Rheumatism 58(8):2228-2235, American college of Rheumatology, United States (2008).
Dominguez-Villar, M., et al., "Regulatory T cells in autoimmune disease," Nature Immunology 19:665-673, Nature America, United States (2018).
Fujita, M., et al., "Pulmonary Hypertension in TNF-$\alpha$-overexpressing mice is associated with decreased VEGF gene expression," J Appl Physiol 93:2162-2170, American Physiological Society, United States (2002).

(56) References Cited

OTHER PUBLICATIONS

Gonzalez, "Adipose-Derived Mesenchymal Stem Cells Alleviate Experimental Colitis by Inhibiting Inflammatory and Autoimmune Responses," Gastroenterology 136(3):978-989, Elsevier, Netherlands (2009).
Gray, J.D., et al., "Generation of an Inhibitory Circuit involving CD8+ T Cells, IL-2 and NK Cell-Derived TGF-β: Contrasting Effects of Anti-CD2 and Anti-CD3," The Journal of immunology 160:2248-2254, American Association of Immunologists, United States (1998).
Gray, J.D., et al., "The Role of Transforming Growth Factor β in the Generation o Suppression: An Interaction Between CD8+ and NK cells," J. Exp. Med. 180:1937-1942, Rockefeller University Press, United States (1994).
Guo, G., et al., "Contributions of angiotensin II and tumor necrosis factor-α to the development of renal fibrosis," Am J. Physiol Renal Physiol 280:F777-F785, American Physiological Society, United States (2001).
Ikehara, S., "A New Concept of Stem Cell Disorders and Their New Therapy," Journal of Hematotherapy & Stem Cell Research 12:643-653, Mary Ann Liebert, United States (2003).
Jiang, H., et al., "An Integrated View of Suppressor T cell Subsets in Immunoregulation," The Journal of Clinical Investigation 114(9): 1198-1208, American Society for Clinical Investigation, United States (2004).
Katzenstein, A-L, A., et al., "Idiopathic Pulmonary Fibrosis; Clinical Relevance of Pathologic Classification," AM J Respir Crit Care Med 157:1301-1315, American Thoracic Society, United States (1998).
Kitamura, A., et al., "Renal Fibroblasts are sensitive to growth-reducing and matrix reducing factors from activated lymphocytes," Clin Exp Immunol 91:516-520, Wiley Online Library, United States (1993).
Kong, Q., et al., "Administration of bone marrow stromal cells ameliorates experimental autoimmune myasthenia gravis by altering the balance of Th1/Th2/Th17/Treg cell subsets through the secretion of TGF-β," Journal of Neuroimmunology 207:83-91, Elsevier, Netherlands (2009).
Levings, M.K., et al., "Human CD25+CD4+ T Suppressor Cell Clones Produce Transofmring Growth Factor β, but not Interleukin 10, and are Distinct from Type 1 T Regulatory Cells," J. Exp Medicine 196(10):1335-1346, Rockefeller University Press, United States (2002).
McNulty, K., et al., "Stem Cells and Pulmonary Fibrosis: Cause or Cure?," Proc Am Thorac Soc 9(3):164-171, American Thoracic Society, United States (2012).
Moudgil, K., et al ., "Cytokines in Autoimmunity: Role in Induction, Regulation, and Treatment," Journal of Interferon & Cytokine Research 31(10):695-703, Mary Ann Liebert, United States (2011).
Muller, D., et al., "Immunosuppressive Treatment Protects Against Angiotensin II-Induced Renal Damage," American Journal of Pathology 161(5):1679-1693, American Society for Investigative Pathology, United States (2002).
Sky Ng, T.H., et al., "Regulation of adaptive immunity; the role of interleukin-10," Frontiers in Immunology 4(129):1-13, Frontiers Media, Switzerland (2013).
Oxford Advanced Learner's Dictionary, Fifth Ed., AS Hornby (ed.), Oxford University Press, 59,812,824 & 825 (2015).
Pantelidis, P., et al., "Tumor necrosis factor-α production in fibrosing aveolitis is macrophage subset specific," Respiratory Research 2(6):365-372, Biomed Central, United Kingdom (2001).
Parronchi, P., et al., "Type 1 T-Helper Cell Predominance and Interleukin-12 Expression in the Gut of Patients with Crohn's Disease," American Journal of Pathology 150(3): 823-832, American Society for Investigative Pathology, United States (1997).
Pereira, R.F., et al., "Cultured adherent cells from marrow can serve as long-lasting precursor cells for bone, cartilage, and lung in irradiated mice," Proc. Natl. Acad. Sci 92:4587-4861, United States National Academy of Sciences, United States (1995).
Piguet, P.F., et al., "Requirement of Tumor necrosis factor for development of silica induced pulmonary fibrosis," Nature 344:245-247, Nature Publising Group, United Kingdom (1990).
Rakebrandt, N., et al., "Regulatory T Cells: balancing protection versus pathology," Swiss Med Wkly 146:w14343, EMH Swiss Medical Publishers, United States (2016).
Rasmusson, I., et al., "Human Mesenchymal stem cells increase interleukin-2 and soluble IL-2 receptor in mixed lymphocyte cultures," Bone Marrow Transplant P431: S87 (2004).
Ruiz, V., et al., "Unbalanced collagenases/TIMP-1 expression and epithelial apoptosis in experimental lung fibrosis," Am J Physiol Lung Cell Mol Physiol 285:L1026-L1036, American Physiological Society, United States (2003).
Semedo, P., et al., "Mesenchymal Stem Cells Attenuate Renal Fibrosis through Immune Modulation and Remodeling Properties in a Rat Remnant Kidney Model," Stem Cells 27:3063-3073, Wiley Online Library, United States (2009).
Shevach, E.M., "Regulatory/Suppressor T Cells in Health and Disease," Arthritis & Rheumatism 50(9):2721-2724, Wiley Online Library, United States (2004).
Sime, P.J., et al., "Transfer of Tumor Necrosis Factor-α to Rat Lung Induces Severe Pulmonary Inflammation and Patch Interstitial Fibrogenesis with Induction of Transforming Growth Factor β1 and Myofibroblasts," American Journal of Pathology 153(3):825-832, American Society for Investigative Pathology, United States (1998).
Ullah, I., et al., "Human mesenchymal stem cells—current trends and future prospective," Bioscience Reports 35:e00191, Springer, United States (2015).
Usuiner, B., et al., "Management of Fibrosis: The Mesenchymal Stromal Cells Breakthrough," Stem Cells International 2014: 26 pp. , Hindawi Publishing Corporation, Egypt (2014).
Viglietta, V., et al., Loss of Functional Suppression by CD4+CD25+ Regulatory T Cells in Patients with Multiple Sclerosis, J. Exp. Med 199(7):971-979, Rockefeller University Press, United States (2004).
Yamagiwa, S., et al., "A Role for TGF-β in the Generation and Expansion of CD4+CD25+ Regulatory T Cells from Human Peripheral Blood," The Journal of Immunology(166):7282-7289, American Association of Immunologists, United States (2001).
Zappia, E., et al., "Mesenchymal stem cells ameliorate experimental autoimmune encephalomyelitis inducing T-cell energy," Immunobiology Blood 106(5):1755-1761, American Society of Hematology, United States (2005).
Diegelmann; R.F. et al., "Wound Healing: An Overview of Acute, Fibrotic and Delayed Healing," Frontiers in Bioscience 9:283-9, *Frontiers in Bioscience*, United States (Jan. 2004).
Gonzalez; A.C.O. et al., "Wound Healing—A literature review," *An Bras Dermatol* 91(5): 614-20, Sociedade Brasileira de Dermatologia, Brazil (2016).
Koh; T.J. et al., "Inflammation and wound healing: The role of the macrophage," *Expert Rev Mol Med* 13: e23, Cambridge University Press, England (2013).
Hackney, J.A., et al., "A molecular profile of a hematopoietic stem cell niche," *PNAS*, 99(20): 13061-13066, National Academy of Press, United States (2002).
Office Action dated Nov. 19, 2019, in U.S. Appl. No. 16/206,235, Aggarwal, S., filed Nov. 30, 2018, 23 pages.
Ploemacher, R.E., et al., "An in vitro limiting-dilution assay of long-term repopulating hematopoietic stem cells in the mouse," *Blood*, 74(8): 2755-2763, American Society of Hematology, United States (1989).
Serezani, A.Pm., et al., "IL-4 impairs wound healing potential in the skin by repressing fibronectin expression," *Journal of Allergy and Clinical Immunology*,139(1): 142-151, Elsevier, Netherlands (2017).
Office Action dated Sep. 10, 2019, in U.S. Appl. No. 14/138,577, Aggarwal, S., filed Dec. 23, 2013, 13 pages.
Bouma, G., et al., "The Immunological and genetic basis of inflammatory bowel disease," *Nature Reviews Immunology*, 3:521-533, Nature Publishing Group, United Kingdom (Jul. 2003).
Breitbach, M., et al., "Potential risks of bone marrow cell transplantation into infarcted Hearts," *Blood*, 110(4): 1362-1369, The American Society of Hematology, United States (Aug. 15, 2007).
Co-pending U.S. Appl. No. 16/811,900, inventors Aggarwal, S., et al., filed Mar. 6, 2020 (Not Published).

(56) References Cited

OTHER PUBLICATIONS

Co-pending U.S. Appl. No. 16/815,784, inventors Aggarwal, S., et al., filed Mar. 11, 2020 (Not Published).
Declaration of Professor Dr. Hans-Dieter Volk, in Opposition Proceedings regarding EP 2,298,864 B, 7 pages.
Declaration of Professor Ornella Parolini, in Opposition Proceedings regarding EP 2,298,864 B, 47 pages.
Djouad, F. et al. "Mesenchymal Stem Cells Inhibit the Differentiation of Dendritic Cells Through an Interleukin-6-Dependent Mechanism," *Stem Cells*, 25: 2025-2032, Alpha Med Press, United States (2007).
Eming, S.A. et al., "Accelerated Wound Closure in Mice Deficient for Interleukin-10," *The American Journal of Pathology* 170(1):188-202, American Society for Investigative Pathology, United States (2007).
Janssen, S., et al. "Autologous bone marrow-derived stem-cell transfer in patients with ST-segment elevation myocardial infarction: double-blind, randomised controlled trial," *The Lancet*, 367(9505): P113-121, Elsevier, Inc., Netherlands (Jan. 14, 2006).
Leibovich, S.J. and Ross; R., "The Role of the Macrophage in Wound Repair," *The American Journal of Pathology*, 78(1):71-100, American Society for Investigative Pathology, United States (1975).
Li, Y., et al. "Marrow stromal cell transplantation in stroke and traumatic brain injury," *Neurosci. Lett*, 456(3): 120-123, Elsevier Ireland Ltd., Ireland (Jun. 12, 2009).
Moroguchi, A. et al., "Interleukin-10 Supresses proliferation and remodeling of extracellular matrix of cultured human skin fibroblasts," *European Surgical Research*, 36:39-44, Karger Publications, England (Jan. to Feb. 2004).
McIntosh, K. and Bartholomew, A., "Stromal Cell Modulation of The Immune System," *Graft Review*, 3(6):324-8, SAGE Publications, United States (2000).
McKenna, K. et al., "Plasmacytoid Dendritic Cells: Linking Innate and Adaptive Immunity," *Journal of Virology*, 79(1): 17-27, American Society for Microbiology, United States (2005).
Notice of Allowance dated Jan. 23, 2020, in U.S. Appl. No. 14/138,577, Aggarwal, S., filed Dec. 23, 2013, 10 pages.
Notice of Allowance dated Apr. 22, 2020, in U.S. Appl. No. 16/206,235, Aggarwal, S., filed Nov. 30, 2018, 7 pages.
Pittenger, M.F., and Martin, B.J., "Mesenchymal Stem Cells and Their Potential as Cardiac Therapeutics," *Circ. Res*, 95: 9-20, American Heart Association, United States (2004).
Rankin; J.A., "Biological Mediators of Acute Inflammation," *AACN Clinical Issues*, 15(1):3-17, American Association of Critical-Care Nurses, United States (Jan. 2004).
Tomita, S., et al., "The Use of Bone Marrow Mesenchymal Stem Cells to Repair the Infarcted Heart," *Cardiac Remodeling and Failure*, pp. 345-354, Kluwer Academic Publishers, United States (2003).
Suuronen, E.J., et al., "Comparative effects of mesenchymal progenitor cells, endothelial progenitor cells, or their combination on myocardial infarct regeneration and cardiac function," *J. Thorac Cardiovasc Surg.*, 134(5): 1249-58, The American Association for Thoracic Surgery, United States (2007).
Tremain, N. et al., "MicroSAGE Analysis of 2,353 Expressed Genes In A Single Cell-Derived Colony Of Undifferenctiated Human Mesenchymal Stem Cells Reveals Mrnas Of Multiple Cell Lineages," *Stem Cells*, 19:408-18, Alpha Med Press, United States (2001).
Yilmaz, G., et al., "Induction of neuro-protective/regenerative genes in stem cells infiltrating post-ischemic bran tissue," *Experimental & Translational Stroke Medicine*, 2(11): 1-10, BioMed Central Ltd., United Kingdom (2010).
Zacharek, A., et al., "Angiopoietin1/Tie2 and VEGF/Flk1 induced by MSC treatment amplifies angiogenesis and vascular stabilization after stroke," *J. Cereb. Blood Flow Metab*, 27(10): 1684-1691, SAGE Publishing, United States (Oct. 2007).
Chen, J., et al., "Intravenous Administration of Human Bone Marrow Stromal Cells Induces Angiogenesis in the Ischemic Boundary Zone After Stroke in Rats," *Circulation Research*, 92:692-699, American Heart Association, Inc., United States (2003).
Kinnaird, T., et al., "Local Delivery of Marrow-Derived Stromal Cells Augments Collateral Perfusion Through Paracrine Mechanisms," *Circulation*, 109:1543-1549, American Heart Association, United States (Mar. 2004).
Guoping, A., et al., "Effects of bone marrow mesenchymal stem cells on healing of wound combined with local radiation injury," *Chinese Journal of Radiological Medicine and Protection*, 22(3): 164-167, Oriprobe Information Services, Inc., China (2002).
Office Action dated Feb. 1, 2019, in U.S. Appl. No. 14/138,577, Aggarwal, S., et al., filed Dec. 23, 2013.
EP Communication for European Application No. 10011224.2, European Patent Office, Munich, Germany, dated Feb. 25, 2019, 5 pages.
EP Communication for European Application No. 14172807.1, European Patent Office, Munich, Germany, dated Mar. 3, 2019, 6 pages.
Al-Khaldi, A.A., et al., "VEGF-Dependent Angiogenic Response Induced by Ex-Vivo Cultured Marrow Stromal Cells," *Scientific Sessions*, Abstract 594, 1 page (2001).
Aurbach, R., et al., "Angiogenesis Assays: A Critical Overview," *Clinical Chemistry* 4:1, pp. 32-40, American Association for Clinical Chemistry, United States (2003).
Cebe-Suarez, S., et al., "The role of VEGF receptors in angiogenesis; complex partnerships," *Cell. Mol. Life Sci.*, 63:601-615, Birkhäuser Verlag, Basel (2006).
Cimpean, A-M., "A brief history of angiogenesis assays," *Int. J. Dev. Biol.*, 55:377-385, UBC Press, Spain (2011).
Ferrara, N., "Vascular Endothelial Growth Factor: Basic Science and Clinical Progress," *Endocrine Reviews*, 25(4):581-611, The Endocrine Society, United States (Aug. 2004).
Kaigler, D., et al., "Role of Vascular Endothelial Growth Factor in Bone Marrow Stromal Cell Modulation of Endothelial Cells," *Tissue Engineering*, vol. 9, No. 1, pp: 95-112, Mary Ann Liebert, Inc., United States (2003).
Khouri, E.M., et al., "Flow in the Major Branches of the Left Coronary Artery during Experimental Coronary Insufficiency in the Unanesthetized Dog," *Circulation Research*, vol. XXIII, pp. 99-110, Lippincott Williams & Wilkins, United States (1968).
Kinnaird, T., et al., "Marrow-Derived Stromal Cells Express Genes Encoding a Broad Spectrum of Arteriogenic Cytokines and Promote in Vitro and in Vivo Arteriogenesis Through Paracrine Mechanisms," *Cir Res.*, 94:678-685, American Heart Association, United States (Jan. 2004).
Kinnaird, T., et al., "Marrow-Derived Stromal Cells Express Genes Encoding a Broad Spectrum of Arteriogenic Cytokines and Promote in Vitro and in Vivo Arteriogenesis Through Paracrine Mechanisms," *PubMed*, Abstract, 2 pages (Jan. 2004).
Lindner, U., et al., "Mesenchymal Stem or Stromal Cells: Toward a Better Understanding of Their Biology?," *Transfus Med Hemother*, 37:75-83, Karger GmbH, Freiburg (2010).
Nowak-Sliwinska, P., et al., "Consensus guidelines for the use and interpretation of angiogenesis assays," *Angiogenesis*, vol. 21:3, pp. 425-532, Springer, Germany (2018).
Oxford Dictionary definition for Angiogenesis, available online at https://en.oxforddictionaries.com/definition/angiogenesis, 4 pages (2018).
Le Blanc, K., et al., "Immunomodulatory effects of fetal and adult mesenchymal stem cells," *Cytotherapy*, 5(6):485-489, (2003).
Staton, C.A., et al., "A critical analysis of current in vitro and in vivo angiogenesis assays," *Int. J. Exp. Path.*, 90:195-221, Blackwell Publishing Ltd., United States (2009).
Barry; FP and Murphy; JM, "Mesenchymal stem cells: clinical application and biological characterization," *Intl J of Biochemistry & Cell Biology* 36:568-84, Elsevier, Netherlands (Apr. 2004).
Sherer and Shoenfeld, "Autoimmune diseases and autoimmunity post-bone marrow transplantation," *Bone Marrow Transplantation* 22:873-81, Stockton Press, England (1998).
Lazarus; H., "Role of mesenchymal stem cells (MSC) in allogeneic transplantation: Early phase I clinical results," *Blood* 96:392a, abstract 1691 (2000).

(56) References Cited

OTHER PUBLICATIONS

Moore; BB and Hogaboam; CM, "Murine models of pulmonary fibrosis," *American Journal of Physiology-Lung Cellular and Molecular Physiology* 36:568-84, American Physiological Society, United States (2004).

* cited by examiner

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: synthetic sequences and are primers for PCR
      derived from human COX-1
<220> FEATURE:
<221> NAME/KEY: misc_feature
<222> LOCATION: (1)..(22)
<223> OTHER INFORMATION: COX-1 forward primer

<400> SEQUENCE: 1
ccggatgcca gtcaggatga tg                                              22

<210> SEQ ID NO 2
```

-continued

```
<211> LENGTH: 22
<212> TYPE: DNA
<213> ORGANISM: Artificial Sequence
<220> FEATURE:
<223> OTHER INFORMATION: synthetic sequences and are primers for PCR
      derived from human COX-1
<220> FEATURE:
<221> NAME/KEY: misc_feature
<222> LOCATION: (1)..(22)
<223> OTHER INFORMATION: COX-1 reverse primer

<400> SEQUENCE: 2
ctagacagcc agatgctgac ag                                              22

<210> SEQ ID NO 3
<211> LENGTH: 20
<212> TYPE: DNA
<213> ORGANISM: Artificial Sequence
<220> FEATURE:
<223> OTHER INFORMATION: synthetic sequences and are primers for PCR
      derived from human COX-2
<220> FEATURE:
<221> NAME/KEY: misc_feature
<222> LOCATION: (1)..(20)
<223> OTHER INFORMATION: COX-2 forward primer

<400> SEQUENCE: 3
atctaccctc ctcaagtccc                                                 20

<210> SEQ ID NO 4
<211> LENGTH: 21
<212> TYPE: DNA
<213> ORGANISM: Artificial Sequence
<220> FEATURE:
<223> OTHER INFORMATION: primer for PCR derived from human COX-2
<220> FEATURE:
<221> NAME/KEY: misc_feature
<222> LOCATION: (1)..(21)
<223> OTHER INFORMATION: COX-2 reverse primer

<400> SEQUENCE: 4
taccagaagg gcaggataca g                                               21
```

MESENCHYMAL STEM CELLS AND USES THEREFOR

RELATED APPLICATIONS

This application is a continuation of U.S. patent application Ser. No. 14/138,577, filed on Dec. 23, 2013, which is a continuation of U.S. patent application Ser. No. 13/222,778, filed on Aug. 31, 2011, now abandoned, which is a continuation of U.S. patent application Ser. No. 12/908,119, filed on Oct. 20, 2010, now abandoned, which is a continuation of U.S. patent application Ser. No. 11/541,853, filed on Oct. 2, 2006, now abandoned, which is a continuation-in-part of U.S. patent application Ser. No. 11/080,298, filed on Mar. 15, 2004, now abandoned, which claims priority based on U.S. Provisional Patent Application Ser. No. 60/555,118, filed on Mar. 22, 2004, the contents of which are incorporated by reference in their entireties.

SEQUENCE LISTING

The instant application contains a sequence listing which has been submitted electronically in ASCII format and is hereby incorporated by reference in its entirety. Said ASCII copy, created on Nov. 29, 2018, is named 3944_019000J_SeqListing_ST25.txt and is 1,822 bytes in size.

FEDERALLY SPONSORED RESEARCH OR DEVELOPMENT

The invention was made with Government support under Contract No. N66001-02-C-8068 awarded by the Department of the Navy. The Government has certain rights in this invention.

BACKGROUND OF THE INVENTION

This invention relates to mesenchymal stem cells. More particularly, this invention relates to novel uses for mesenchymal stem cells, including promoting angiogenesis in various tissues and organs, treating autoimmune diseases, treating allergic responses, treating cancer, treating inflammatory diseases and disorders, promoting would healing, treating inflammation, and repairing epithelial damage.

Mesenchymal stem cells (MSCs) are multipotent stem cells that can differentiate readily into lineages including osteoblasts, myocytes, chondrocytes, and adipocytes (Pittenger, et al., *Science, Vol.* 284, pg. 143 (1999); Haynesworth, et al., *Bone*, Vol. 13, pg. 69 (1992); Prockop, *Science*, Vol. 276, pg. 71 (1997)). In vitro studies have demonstrated the capability of MSCs to differentiate into muscle (Wakitani, et al., Muscle Nerve, Vol. 18, pg. 1417 (1995)), neuronal-like precursors (Woodbury, et al., *J. Neurosci. Res.*, Vol. 69, pg. 908 (2002); Sanchez-Ramos, et al., *Exp. Neurol.*, Vol. 171, pg. 109 (2001)), cardiomyocytes (Toma, et al., *Circulation*, Vol. 105, pg. 93 (2002); Fakuda, *Artif. Organs*, Vol. 25, pg. 187 (2001)) and possibly other cell types. In addition, MSCs have been shown to provide effective feeder layers for expansion of hematopoietic and embryonic stem cells (Eaves, et al., *Ann. N.Y. Acad. Sci.*, Vol. 938, pg. 63 (2001); Wagers, et al., *Gene Therapy*, Vol. 9, pg. 606 (2002)). Recent studies with a variety of animal models have shown that MSCs may be useful in the repair or regeneration of damaged bone, cartilage, meniscus or myocardial tissues (DeKok, et al., *Clin. Oral Implants Res.*, Vol. 14, pg. 481 (2003)); Wu, et al., *Transplantation*, Vol. 75, pg. 679 (2003); Noel, et al., *Curr. Opin. Investig. Drugs*, Vol. 3, pg. 1000 (2002); Ballas, et al., *J. Cell. Biochem. Suppl.*, Vol. 38, pg. 20 (2002); Mackenzie, et al., *Blood Cells Mol. Dis.*, Vol. 27 (2002)). Several investigators have used MSCs with encouraging results for transplantation in animal disease models including osteogenesis imperfecta (Pereira, et al., *Proc. Nat. Acad. Sci.*, Vol. 95, pg. 1142 (1998)), parkinsonism (Schwartz, et al., *Hum. Gene Ther.*, Vol. 10, pg. 2539 (1999)), spinal cord injury (Chopp, et al., *Neuroreport*, Vol. 11, pg. 3001 (2000); Wu, et al., *J. Neurosci. Res.*, Vol. 72, pg. 393 (2003)) and cardiac disorders (Tomita, et al., *Circulation*, Vol. 100, pg. 247 (1999). Shake, et al., *Ann. Thorac. Surg.*, Vol. 73, pg. 1919 (2002)). Importantly, promising results also have been reported in clinical trials for osteogenesis imperfecta (Horwitz, et al., *Blood*, Vol. 97, pg. 1227 (2001); Horowitz, et al. *Proc. Nat. Acad. Sci.*, Vol. 99, pg. 8932 (2002)) and enhanced engraftment of heterologous bone marrow transplants (Frassoni, et al., *Int. Society for Cell Therapy*, SA006 (abstract) (2002); Koc, et al., *J. Clin. Oncol.*, Vol. 18, pg. 307 (2000)).

MSCs express major histocompatibility complex (MHC) class I antigen on their surface but do not express MHC class II (Le Blanc, et al., *Exp. Hematol.*, Vol. 31, pg. 890 (2003); Potian, et al., *J. Immunol.*, Vol. 171, pg. 3426 (2003)) and no B7 or CD40 co-stimulatory molecules (Majumdar, et al., *J. Biomed. Sci.*, Vol. 10, pg. 228 (2003)), suggesting that these cells have a low-immunogenic phenotype (Tse, et al., *Transplantation*, Vol. 75, pg. 389 (2003)). MSCs also inhibit T-cell proliferative responses in an MHC-independent manner (Bartholomew, et al., *Exp. Hematol.*, Vol. 30, pg. 42 (2002); Devine, et al., *Cancer J.*, Vol. 7, pg. 576 (2001); DiNicola, et al., *Blood*, Vol. 99, pg. 3838 (2002)). These immunological properties of MSCs may enhance their transplant engraftment and limit the ability of the recipient immune system to recognize and reject allogeneic cells following transplantation. The production of factors by MSCs, that modulate the immune response and support hematopoiesis together with their ability to differentiate into appropriate cell types under local stimuli make them desirable stem cells for cellular transplantation studies (Majumdar, et al., *Hematother. Stem Cell Res.*, Vol. 9, pg. 841 (2000); Haynesworth, et al., *J. Cell. Physiol.*, Vol. 166, pg. 585 (1996).

BRIEF SUMMARY OF THE INVENTION

Applicants presently have examined the interactions of mesenchymal stem cells with isolated immune cell populations, including dendritic cells (DC1 and DC2), effector T-cells (Th1 and Th2), and NK cells. Based on such interactions, Applicants discovered that mesenchymal stem cells may regulate the production of various factors that may regulate several steps in the immune response process. Thus, the mesenchymal stem cells may be employed in the treatment of disease conditions and disorders involving the immune system, or diseases, conditions, or disorders involving inflammation, epithelial damage, or allergic responses. Such diseases, conditions, and disorders include, but are not limited to, autoimmune diseases, allergies, arthritis, inflamed wounds, alopecia araeta (baldness), periodontal diseases including gingivitis and periodontitis, and other diseases, conditions or disorders involving an immune response.

In addition, it is believed that mesenchymal stem cells express and secrete vascular endothelial growth factor, or VEGF, which promotes angiogenesis by stimulating the formation of new blood vessels. Mesenchymal stem cells also stimulate peripheral blood mononuclear cells (PBMCs) to produce VEGF.

Furthermore, it is believed that mesenchymal stem cells stimulate dendritic cells (DCs) to produce Interferon-Beta (IFN-β), which promotes tumor suppression and immunity against viral infection.

DETAILED DESCRIPTION OF THE INVENTION

In accordance with an aspect of the present invention, there is provided a method of treating a disease selected from the group consisting of autoimmune diseases and graft-versus-host disease in an animal. The method comprises administering to the animal mesenchymal stem cells in an amount effective to treat the disease in the animal.

Although the scope of this aspect of the present Invention is not to be limited to any theoretical reasoning, it is believed that at least one mechanism by which the mesenchymal stem cells suppress autoimmune disease and graft-versus-host disease is by causing the release of Interleukin-10 (IL-10) from regulatory T-cells ($T_{res}$ cells) and/or dendritic cells (DC).

Autoimmune diseases which may be treated in accordance with the present invention include, but are not limited to, multiple sclerosis, Type 1 diabetes, rheumatoid arthritis, uveitis, autoimmune thyroid disease, inflammatory bowel disease, scleroderma, Graves' Disease, lupus, Crohn's disease, autoimmune lymphoproliferative disease (ALPS), demyelinating disease, autoimmune encephalomyelitis, autoimmune gastritis (AIG), and autoimmune glomerular diseases. Also, as noted hereinabove, graft-versus-host disease may be treated. It is to be understood, however, that the scope of the present invention is not to be limited to the treatment of the specific diseases mentioned herein.

In one embodiment, the animal to which the mesenchymal stem cells are administered is a mammal. The mammal may be a primate, including human and non-human primates.

In general, the mesenchymal stem cell (MSC) therapy is based, for example, on the following sequence: harvest of MSC-containing tissue, isolation and expansion of MSCs, and administration of the MSCs to the animal, with or without biochemical or genetic manipulation.

The mesenchymal stem cells that are administered may be a homogeneous composition or may be a mixed cell population enriched in MSCs. Homogeneous mesenchymal stem cell compositions may be obtained by culturing adherent marrow or periosteal cells, and the mesenchymal stem cell compositions may be obtained by culturing adherent marrow or periosteal cells, and the mesenchymal stem cells may be identified by specific cell surface markers which are identified with unique monoclonal antibodies. A method for obtaining a cell population enriched in mesenchymal stem cells is described, for example, in U.S. Pat. No. 5,486,359. Alternative sources for mesenchymal stem cells include, but are not limited to, blood, skin, cord blood, muscle, fat, bone, and perichondrium.

Compositions having greater than about 95%, usually greater than about 98%, of human mesenchymal stem cells can be achieved using techniques for isolation, purification, and culture expansion of mesenchymal stem cells. For example, isolated, cultured mesenchymal stem cells may comprise a single phenotypic population (about 95% or about 98% homogeneous) by flow cytometric analysis of expressed surface antigens. The desired cells in such composition are identified as expressing a cell surface marker (e.g., CD73 or CD105) specifically bound by an antibody produced from hybridoma cell line SH2, ATCC accession number HB 10743; an antibody produced from hybridoma cell line SH3, ATCC accession number HB 10744; or an antibody produced from hybridoma cell line SH4, ATCC accession number HB 10745.

The mesenchymal stem cells may be administered by a variety of procedures. The mesenchymal stem cells may be administered systemically, such as by intravenous, intraarterial, or intraperitoneal administration.

The mesenchymal stem cells may be from a spectrum of sources including autologous, allogeneic, or xenogeneic.

The mesenchymal stem cells are administered in an amount effective to treat an autoimmune disease or graft-versus-host disease in an animal. The mesenchymal stem cells may be administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$·cells/kg. The amount of mesenchymal stem cells to be administered is dependent upon a variety of factors, including the age, weight, and sex of the patient, the autoimmune disease to be treated, and the extent and severity thereof.

The mesenchymal stem cells may be administered in conjunction with an acceptable pharmaceutical carrier. For example, the mesenchymal stem cells may be administered as a cell suspension in a pharmaceutically acceptable liquid medium or gel for injection or topical application.

In accordance with another aspect of the present invention, there is provided a method of treating an inflammatory response in an animal. The method comprises administering to the animal mesenchymal stem cells in an amount effective to treat the inflammatory response in the animal.

Although the scope of this aspect of the present invention is not to be limited to any theoretical reasoning, it is believed that the mesenchymal stem cells promote T-cell maturation to regulatory T-cells ($T_{reg}$), thereby controlling inflammatory responses. It is also believed that the mesenchymal stem cells inhibit T helper 1 cells (Th1 cells), thereby decreasing the expression of the Interferon-γ, (IFN-γ) in certain inflammatory reactions, such as those associated with psoriasis, for example.

In one embodiment, the inflammatory responses which may be treated are those associated with psoriasis.

In another embodiment, the mesenchymal stem cells may be administered to an animal such that the mesenchymal stem cells contact microglia and/or astrocytes in the brain to reduce inflammation, whereby the mesenchymal stem cells limit neurodegeneration caused by activated glial cells in diseases, or disorders such as Alzheimer's Disease, Parkinson's Disease, stroke, or brain cell injuries.

In yet another embodiment, the mesenchymal stem cells may be administered to an animal such that the mesenchymal stem cells contact keratinocytes and Langerhans cells in the epidermis of the skin to reduce inflammation as may occur in psoriasis, chronic dermatitis, and contact dermatitis. Although this embodiment is not to be limited to any theoretical reasoning, it is believed that the mesenchymal stem cells may contact the keratinocytes and Langerhans cells in the epidermis, and alter the expression of T-cell receptors and cytokine secretion profiles, leading to decreased expression of tumor necrosis factor-alpha (TNF-α) and increased regulatory T-cell ($T_{reg}$ cell) population.

In a further embodiment, the mesenchymal stem cells may be used to reduce inflammation in the bone, as occurs in arthritis and arthritis-like conditions, including but not limited to, osteoarthritis and rheumatoid arthritis, and other arthritic diseases listed in the website www.arthritis.org/conditions/diseases. Although the scope of this embodiment is not intended to be limited to any theoretical reasoning, it is believed that the mesenchymal stem cells may inhibit Interleukin-17 secretion by memory T-cells in the synovial fluid.

In another embodiment, the mesenchymal stem cells may be used to limit inflammation in the gut and liver during Inflammatory bowel disease and chronic hepatitis, respectively. Although the scope of this aspect of the present invention is not intended to be limited to any theoretical reasoning, it is believed that the mesenchymal stem cells promote increased secretion of Interleukin-10 (IL-10) and the generation of regulatory T-cells ($T_{reg}$ cells).

In another embodiment, the mesenchymal stem cells may be used to inhibit excessive neutrophil and macrophage activation in pathological conditions such as sepsis and trauma, including burn injury, surgery, and transplants. Although the scope of this embodiment is not to be limited to any theoretical reasoning, it is believed the mesenchymal stem cells promote secretion of suppressive cytokines such as IL-10, and inhibit macrophage migration inhibitory factor.

In another embodiment, the mesenchymal stem cells may be used to control inflammation in immune privileged sites such as the eye, including the cornea, lens, pigment epithelium, and retina, brain, spinal cord, pregnant uterus and placenta, ovary, testes, adrenal cortex, liver, and hair follicles. Although the scope of this embodiment is not to be limited to any theoretical reasoning, it is believed that the mesenchymal stem cells promote the secretion of suppressive cytokines such as IL-10 and the generation of $T_{reg}$ cells.

In yet another embodiment, the mesenchymal stem cells may be used to treat tissue damage associated with end-stage renal disease (ESRD) infections during dialysis and/or glomerulonephritis. Although the scope of this embodiment is not to be limited to any theoretical reasoning, it is believed that mesenchymal stem cells may promote renal repair. Mesenchymal stem cells also express and secrete vascular endothelial growth factor, or VEGF, which stimulates new blood vessel formation, which should aid in the repair of damaged kidney tissue.

In a further embodiment, the mesenchymal stem cells may be used to control viral infections such as influenza, hepatitis C, Herpes Simplex Virus, vaccinia virus infections, and Epstein-Barr virus. Although the scope of this embodiment is not to be limited to any theoretical reasoning, it is believed that the mesenchymal stem cells promote the secretion of Interferon-Beta (IFN-β).

In yet another embodiment, the mesenchymal stem cells may be used to control parasitic infections such as *Leishmania* infections and *Helicobacter* infections. Although the scope of this embodiment is not to be limited to any theoretical reasoning, it is believed that the mesenchymal stem cells mediate responses by T helper 2 (Th2) cells, and thereby promote increased production of Immunoglobulin E (IgE) by β-cells.

It is to be understood, however, that the scope of this aspect of the present invention is not to be limited to the treatment of any particular inflammatory response.

The mesenchymal stem cells may be administered to a mammal, including human and non-human primates, as hereinabove described.

The mesenchymal stem cells also may be administered systemically, as hereinabove described. Alternatively, in the case of osteoarthritis or rheumatoid arthritis, the mesenchymal stem cells may be administered directly to an arthritic joint.

The mesenchymal stem cells are administered in an amount effective to treat an inflammatory response in an animal. The mesenchymal stem cells may be administered in an amount of from about $1 \times 10^5$ cells/kg to about $1 \times 10^7$ cells/kg. In another embodiment, the mesenchymal stem cells are administered in an amount of from about $1 \times 10^6$ cells/kg to about $5 \times 10^6$ cells/kg. The exact dosage of mesenchymal stem cells to be administered is dependent upon a variety of factors, including the age, weight, and sex of the patient, the inflammatory response being treated, and the extent and severity thereof.

The mesenchymal stem cells may be administered in conjunction with an acceptable pharmaceutical carrier, as hereinabove described.

In accordance with another aspect of the present invention, there is provided a method of treating inflammation and/or repairing epithelial damage in an animal. The method comprises administering to the animal mesenchymal stem cells in an amount effective to treat the inflammation and/or epithelial damage in the animal.

Although the scope of this aspect of the present invention is not to be limited to any theoretical reasoning, it is believed that the mesenchymal stem cells cause a decrease in the secretion of the pro-inflammatory cytokines TNF-α and Interferon-γ by T-cells, and an increase in the secretion of the anti-inflammatory cytokines Interleukin-10 (IL-10) and Interleukin-4 (IL-4) by T-cells. It is also believed that the mesenchymal stem cells cause a decrease in Interferon-γ secretion by natural killer (NK) cells.

The inflammation and/or epithelial damage which may be treated in accordance with this aspect of the present invention includes, but is not limited to, inflammation and/or epithelial damage caused by a variety of diseases and disorders, including, but not limited to, autoimmune disease, rejection of transplanted organs, burns, cuts, lacerations, and ulcerations, including skin ulcerations and diabetic ulcerations.

In one embodiment, the mesenchymal stem cells are administered to an animal in order to repair epithelial damage resulting from autoimmune diseases, including, but not limited to, rheumatoid arthritis, Crohn's Disease, Type 1 diabetes, multiple sclerosis, scleroderma, Graves' Disease, lupus, inflammatory bowel disease, autoimmune gastritis (AIG), and autoimmune glomerular disease. The mesenchymal stem cells also may repair epithelial damage resulting from graft-versus-host disease (GVHD).

This aspect of the present invention is applicable particularly to the repair of epithelial damage resulting from graft-versus-host disease, and more particularly, to the repair of epithelial damage resulting from severe graft-versus-host disease, including Grades III and IV graft-versus-host disease affecting the skin and/or the gastrointestinal system. Applicants have discovered, in particular, that mesenchymal stem cells, when administered to a patient suffering from severe graft-versus-host disease, and in particular, Grades III and IV gastrointestinal graft-versus-host disease, the administration of the mesenchymal stem cells resulted in repair of skin and/or ulcerated intestinal epithelial tissue in the patient.

In another embodiment, the mesenchymal stem cells are administered to an animal in order to repair epithelial damage to a transplanted organ or tissue including, but not limited to, kidney, heart, and lung, caused by rejection of the transplanted organ or tissue.

In yet another embodiment, the mesenchymal stem cells are administered to an animal to repair epithelial damage caused by burns, cuts, lacerations, and ulcerations, including, but not limited to, skin ulcerations and diabetic ulcerations.

The mesenchymal stem cells may be administered to a mammal, including human and non-human primates, as hereinabove described.

The mesenchymal stem cells also may be administered systemically, as hereinabove described.

The mesenchymal stem cells are administered in an amount effective to repair epithelial damage in an animal. The mesenchymal stem cells may be administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact dosage of mesenchymal stem cells to be administered is dependent upon a variety of factors, including the age, weight, and sex of the patient, the type of epithelial damage being repaired, and the extent and severity thereof.

In accordance with yet another aspect of the present invention, there is provided a method of treating cancer in an animal. The method comprises administering to the animal mesenchymal stem cells in an amount effective to treat cancer in the animal.

Although the scope of this aspect of the present invention is not to be limited to any theoretical reasoning, it is believed that the mesenchymal stem cells interact with dendritic cells, which leads to IFN-r3 secretion, which in turn acts as a tumor suppressor. Cancers which may be treated include, but are not limited to, hepatocellular carcinoma, cervical cancer, pancreatic cancer, prostate cancer, fibrosarcoma, medullablastoma, and astrocytoma. It is to be understood, however, that the scope of the present invention is not to be limited to any specific type of cancer.

The animal may be a mammal, including human and non-human primates, as hereinabove described.

The mesenchymal stem cells are administered to the animal in an amount effective to treat cancer in the animal. In general, the mesenchymal stem cells are administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact amount of mesenchymal stem cells to be administered is dependent upon a variety of factors, including the age, weight, and sex of the patient, the type of cancer being treated, and the extent and severity thereof.

The mesenchymal stem cells are administered in conjunction with an acceptable pharmaceutical carrier, and may be administered systemically, as hereinabove described. Alternatively, the mesenchymal stem cells may be administered directly to the cancer being treated.

In accordance with still another aspect of the present invention, there is provided a method of treating an allergic disease or disorder in an animal. The method comprises administering to the animal mesenchymal stem cells in an amount effective to treat the allergic disease or disorder in the animal.

Although the scope of this aspect of the present invention is not to be limited to any theoretical reasoning, it is believed that mesenchymal stem cells, when administered after an acute allergic response, provide for inhibition of mast cell activation and degranulation. Also, it is believed that the mesenchymal stem cells downregulate basophil activation and inhibit cytokines such as TNF-α, chemokines such as Interleukin-8 and monocyte chemoattractant protein, or MCP-1, lipid mediators such as leukotrienes, and inhibit main mediators such as histamine, heparin, chondroitin sulfates, and cathepsin.

Allergic diseases or disorders which may be treated include, but are not limited to, asthma, allergic rhinitis, atopic dermatitis, and contact dermatitis. It is to be understood, however, that the scope of the present invention is not to be limited to any specific allergic disease or disorder.

The mesenchymal stem cells are administered to the animal in an amount effective to treat the allergic disease or disorder in the animal. The animal may be a mammal. The mammal may be a primate, including human and non-human primates. In general, the mesenchymal stem cells are administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact dosage is dependent upon a variety of factors, including the age, weight, and sex of the patient, the allergic disease or disorder being treated, and the extent and severity thereof.

The mesenchymal stem cells may be administered in conjunction with an acceptable pharmaceutical carrier, as hereinabove described. The mesenchymal stem cells may be administered systemically, such as by intravenous or intraarterial administration, for example.

In accordance with a further aspect of the present invention, there is provided a method of promoting wound healing in an animal. The method comprises administering to the animal mesenchymal stem cells in an amount effective to promote wound healing in the animal.

Although the scope of the present invention is not to be limited to any theoretical reasoning, it is believed that, as mentioned hereinabove, the mesenchymal stem cells cause $T_{reg}$ cells and dendritic cells to release Interleukin-10 (IL-10). The IL-10 limits or controls inflammation in a wound, thereby promoting healing of a wound.

Furthermore, the mesenchymal stem cells may promote wound healing and fracture healing by inducing secretion factors by other cell types. For example, the mesenchymal stem cells may induce prostaglandin E2 ($PGE_2$)-mediated release of vascular endothelial growth factor (VEGF) by peripheral blood mononuclear cells (PBMCs), as well as $PGE_2$-mediated release of growth hormone, insulin, insulin-like growth factor 1 (IGF-1) insulin-like growth factor binding protein-3 (IGFBP-3), and endothelin-1.

Wounds which may be healed include, but are not limited to, those resulting from cuts, lacerations, burns, and skin ulcerations.

The mesenchymal stem cells are administered to the animal in an amount effective to promote wound healing in the animal. The animal may be a mammal, and the mammal may be a primate, including human and non-human primates. In general, the mesenchymal stem cells are administered in an amount of from about $1\times10^5$ cells/kg to about $1\times10^7$ cells/kg. In another embodiment, the mesenchymal stem cells are administered in an amount of from about $1\times10^6$ cells/kg to about $5\times10^6$ cells/kg. The exact amount of mesenchymal stem cells to be administered is dependent upon a variety of factors, including the age, weight, and sex of the patient, and the extent and severity of the wound being treated.

The mesenchymal stem cells may be administered in conjunction with an acceptable pharmaceutical carrier, as hereinabove described. The mesenchymal stem cells may be administered systemically, as hereinabove described. Alternatively, the mesenchymal stem cells may be administered directly to a wound, such as in a fluid on a dressing or reservoir containing the mesenchymal stem cells.

In accordance with yet another aspect of the present invention, there is provided a method of treating or preventing fibrosis in an animal. The method comprises administering to the animal mesenchymal stem cells in an amount effective to treat or prevent fibrosis in an animal.

The mesenchymal stem cells may be administered to the animal in order to treat or prevent any type of fibrosis in the animal, including, but not limited to, cirrhosis of the liver, fibrosis of the kidneys associated with end-stage renal disease, and fibrosis of the lungs, including, but not limited to, Acute Respiratory Diseases Syndrome (ARDS) and chronic obstructive pulmonary disease (COPD). It is to be understood that the scope of the present invention is not to be limited to any specific type of fibrosis.

The mesenchymal stem cells are administered to the animal in an amount effective to treat or prevent fibrosis in the animal. The animal may be a mammal, and the mammal may be a primate, including human and non-human primates. In general, the mesenchymal stem cells are administered in an amount of from about $1 \times 10^5$ cells/kg to about $1 \times 10^7$ cells/kg. In another embodiment, the mesenchymal stem cells are administered in an amount of from about $1 \times 10^6$ cells/kg to about $5 \times 10^6$ cells/kg. The exact amount of mesenchymal stem cells to be administered is dependent upon a variety of factors, including the age, weight, and sex of the patient, and the extent and severity of the fibrosis being treated or prevented.

The mesenchymal stem cells may be administered in conjunction with an acceptable pharmaceutical carrier, as hereinabove described. The mesenchymal stem cells may be administered systemically, also as hereinabove described.

It is another object of the present invention to promote angiogenesis in a tissue or organ of an animal, wherein such tissue or organ is in need of angiogenesis.

Thus, in accordance with a further aspect of the present invention, there is provided a method of promoting angiogenesis in an organ or tissue of an animal. The method comprises administering to the animal mesenchymal stem cells in an amount effective to promote angiogenesis in an organ or tissue of the animal.

Angiogenesis is the formation of new blood vessels from a pre-existing microvascular bed.

The induction of angiogenesis may be used to treat coronary and peripheral artery insufficiency, and thus may be a noninvasive and curative approach to the treatment of coronary artery disease, ischemic heart disease, and peripheral artery disease. Angiogenesis may play a role in the treatment of diseases and disorders in tissue and organs other than the heart, as well as in the development and/or maintenance of organs other than the heart. Angiogenesis may provide a role in the treatment of internal and external wounds, as well as dermal ulcers. Angiogenesis also plays a role in embryo implantation, and placental growth, as well as the development of the embryonic vasculature. Angiogenesis also is essential for the coupling of cartilage resorption with bone formation, and is essential for correct growth plate morphogenesis.

Furthermore, angiogenesis is necessary for the successful engineering and maintenance of highly metabolic organs, such as the liver, where a dense vascular network is necessary to provide sufficient nutrient and gas transport.

The mesenchymal stem cells can be administered to the tissue or organ in need of angiogenesis by a variety of procedures. The mesenchymal stem cells may be administered systemically, such as by intravenous, intraarterial, or intraperitoneal administration, or the mesenchymal stem cells may be administered directly to the tissue or organ in need of angiogenesis, such as by direct injection into the tissue or organ in need of angiogenesis.

The mesenchymal stem cells may be from a spectrum of sources including autologous, allogeneic, or xenogeneic.

Although the scope of the present invention is not to be limited to any theoretical reasoning, it is believed that the mesenchymal stem cells, when administered to an animal, stimulate peripheral blood mononuclear cells (PBMCs) to produce vascular endothelial growth factor, or VEGF, which stimulates the formation of new blood vessels.

In one embodiment, the animal is a mammal. The mammal may be a primate, including human and non-human primates.

The mesenchymal stem cells, in accordance with the present invention, may be employed in the treatment, alleviation, or prevention of any disease or disorder which can be alleviated, treated, or prevented through angiogenesis. Thus, for example, the mesenchymal stem cells may be administered to an animal to treat blocked arteries, including those in the extremities, i.e., arms, legs, hands, and feet, as well as the neck or in various organs. For example, the mesenchymal stem cells may be used to treat blocked arteries which supply the brain, thereby treating or preventing stroke. Also, the mesenchymal stem cells may be used to treat blood vessels in embryonic and postnatal corneas and may be used to provide glomerular structuring. In another embodiment, the mesenchymal stem cells may be employed in the treatment of wounds, both internal and external, as well as the treatment of dermal ulcers found in the feet, hands, legs or arms, including, but not limited to, dermal ulcers caused by diseases such as diabetes and sickle cell anemia.

Furthermore, because angiogenesis is involved in embryo implantation and placenta formation, the mesenchymal stem sells may be employed to promote embryo implantation and prevent miscarriage.

In addition, the mesenchymal stem cells may be administered to an unborn animal, including humans, to promote the development of the vasculature in the unborn animal.

In another embodiment, the mesenchymal stem cells may be administered to an animal, born or unborn, in order to promote cartilage resorption and bone formation, as well as promote correct growth plate morphogenesis.

The mesenchymal stem cells are administered in an amount effective in promoting angiogenesis in an animal. The mesenchymal stem cells may be administered in an amount of from about $1 \times 10^5$ cells/kg to about $1 \times 10^7$ cells/kg. In another embodiment, the mesenchymal stem cells are administered in an amount of from about $1 \times 10^6$ cells/kg to about $5 \times 10^6$ cells/kg. The amount of mesenchymal stem cells to be administered is dependent upon a variety of factors, including the age, weight, and sex of the patient, the disease or disorder to be treated, alleviated, or prevented, and the extent and severity thereof.

The mesenchymal stem cells may be administered in conjunction with an acceptable pharmaceutical carrier. For example, the mesenchymal stem cells may be administered as a cell suspension in a pharmaceutically acceptable liquid medium for injection. Injection can be local, i.e., directly into the tissue or organ in need of angiogenesis, or systemic.

The mesenchymal stem cells may be genetically engineered with one or more polynucleotides encoding a therapeutic agent. The polynucleotides may be delivered to the mesenchymal stem cells via an appropriate expression vehicle. Expression vehicles which may be employed to genetically engineer the mesenchymal stem cells include, but are not limited to, retroviral vectors, adenoviral vectors, and adeno-associated virus vectors.

The selection of an appropriate polynucleotide encoding a therapeutic agent is dependent upon various factors, including the disease or disorder being treated, and the extent and severity thereof. Polynucleotides encoding therapeutic agents, and appropriate expression vehicles are described further in U.S. Pat. No. 6,355,239.

It is to be understood that the mesenchymal stem cells, when employed in the above-mentioned therapies and treatments, may be employed in combination with other therapeutic agents known to those skilled in the art, including, but not limited to, growth factors, cytokines, drugs such as anti-inflammatory drugs, and cells other than mesenchymal stem cells, such as dendritic cells, and may be administered with soluble carriers for cells such as hyaluronic acid, or in combination with solid matrices, such collagen, gelatin, or other biocompatible polymers, as appropriate.

It is to be understood that the methods described herein may be carried out in a number of ways and with various modifications and permutations thereof that are well known in the art. It also may be appreciated that any theories set forth as to modes of action or interactions between cell types should not be construed as limiting this invention in any manner, but are presented such that the methods of the invention can be understood more fully.

BRIEF DESCRIPTION OF SEVERAL VIEWS OF THE DRAWINGS

The invention now will be described with respect to the drawings, wherein.

EXAMPLES

Figure 1A:
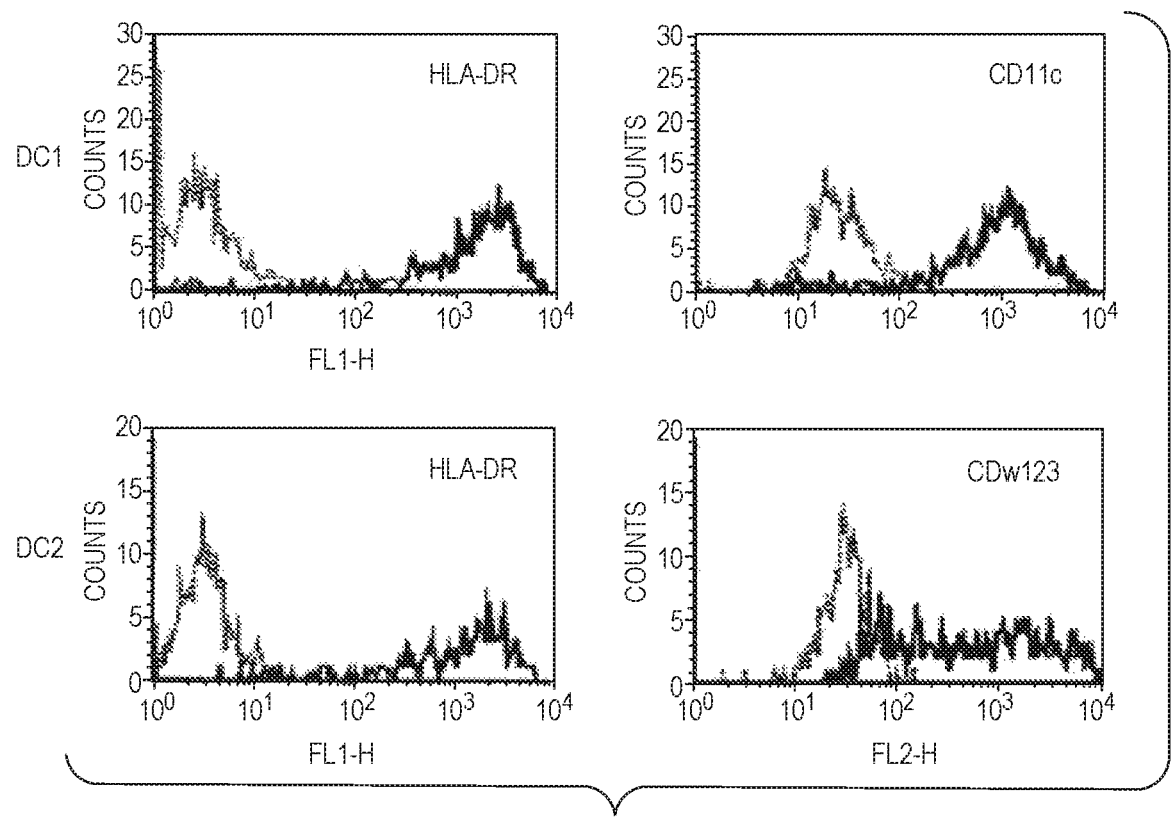
FIGS. 1A-C MSCs modulate dendritic cell functions. (A) Flow cytometric analysis of mature monocytic DC1 cells using antibodies against HLA-DR and CD11c and of plasmacytoid DC2 cells using antibodies against HLA-DR and CD123 (IL-3 receptor). (---): isotype control; (-): FITC/PE conjugated antibodies. (B) MSCs inhibit TNF-α secretion (primary y-axis) and increase IL-10 secretion (secondary y-axis) from activated DC1 and DC2 respectively. (C) MSCs cultured with mature DC1 cells inhibit IFN-γ secretion (primary y-axis) by T cells and increase IL-4 levels (secondary y-axis) as compared to MSC or DC alone. The decreased production of pro-inflammatory IFN-γ and increased production of anti-inflammatory IL-4 in the presence of MSCs indicated a shift in the T cell population towards an anti-inflammatory phenotype.

The invention now will be described with respect to the following examples; it is to be understood, however, that the scope of the present invention is not to be limited thereby.

Example 1

Materials and Methods
Culture of Human MSCs

Human MSCs were cultured as described by Pittenger et al., Science, Vol. 284, pg. 143 (1999). Briefly, marrow samples were collected from the iliac crest of anonymous donors following informed consent by Poietics Technologies, Div of Cambrex Biosciences. MSCs were cultured in complete Dulbecco's Modified Eagle's Medium-Low Glucose (Life Technologies, Carlsbad, Calif.) containing 1% antibiotic-antimyotic solution (Invitrogen, Carlsbad, Calif.) and 10% fetal bovine serum (FBS, JRH BioSciences, Lenexa, Kans.). MSCs grew as an adherent monolayer and were detached with trypsin/EDTA (0.05% trypsin at 37° C. for 3 minutes). All MSCs used were previously characterized for multilineage potential and retained the capacity to differentiate into mesenchymal lineages (chondrocytic, adipogenic, and osteogenic) (Pittenger, et al., Science, Vol. 284, pg. 143 (1999)).

Isolation of Dendritic Cells

Peripheral blood mononuclear cells (PBMCs) were obtained from Poietics Technologies, Div of Cambrex Biosciences (Walkersville, Md.). Precursors of dendritic cells (DCs) of monocytic lineage (CD1c$^+$) were positively selected from PBMCs using a 2-step magnetic separation method according to Dzionek, et al., J. Immunol., Vol. 165, pg. 6037 (2000). Briefly, CD1c expressing B cells were magnetically depleted of CD19$^+$ cells using magnetic beads, followed by labeling the B-cell depleted fraction with biotin-labeled CD1c (BDCA1$^+$) and anti-biotin antibodies and separating them from the unlabeled cell fraction utilizing magnetic columns according to the manufacturer's instructions (Miltenyi Biotech, Auburn, Calif.). Precursors of DCs of plasmacytoid lineage were isolated from PBMCs by immuno-magnetic sorting of positively labeled antibody coated cells (BDCA2$^+$) (Miltenyi Biotech, Auburn, Calif.).

MSC•DC Culture

In most experiments, human MSCs and DCs were cultured in equal numbers for various time periods and cell culture supernatant collected and stored at −80° C. until further evaluation. In selected experiments, MSCs were cultured with mature DC1 or DC2 cells (1:1 MSC:DC ratio) for 3 days, and then the combined cultures (MSCs and DCs) were irradiated to prevent any proliferation. Next, antibody purified, naïve, allogeneic T cells (CD4$^+$,CD45RA$^+$) were added to the irradiated MSCs/DCs and cultured for an additional 6 days. The non-adherent cell fraction (purified T cells) was then collected from the cultures, washed twice and re-stimulated with PHA for another 24 hours, following which cell culture supernatants were harvested and analyzed for secreted IFN-γ and IL-4 by ELISA.

Isolation of NK Cells

Purified populations of NK cells were obtained by depleting non-NK cells that are magnetically labeled with a cocktail of biotin-conjugated monoclonal antibodies (anti-CD3, -CD14, -CD19, -CD36 and anti-IgE antibodies) as a primary reagent and anti-biotin monoclonal antibodies conjugated to Microbeads as secondary labeling reagent. The magnetically labeled non-NK cells were retained in MACS (Miltenyi Biotech, Auburn, Calif.) columns in a magnetic field, while NK cells passed through and were collected.

Isolation of $T_{Reg}$ Cell Population

The $T_{Reg}$ cell population was isolated using a 2-step isolation procedure. First non-CD4$^+$ T cells were indirectly magnetically labeled with a cocktail of biotin labeled antibodies and anti-biotin microbeads. The labeled cells were then depleted by separation over a MACS column (Miltenyi Biotech, Auburn, Calif.). Next, CD4$^+$CD25$^+$ cells were directly labeled with CD25 microbeads and isolated by positive selection from the pre-enriched CD4$^+$ T cell fraction. The magnetically labeled CD4$^+$CD25$^+$ T cells were retained on the column and eluted after removal of the column from the magnetic field.

In order to determine whether the increased CD4+CD25+ population generated in the presence of MSCs were suppressive in nature, CD4+CD25+ $T_{reg}$ cell populations were isolated from PBMC or MSC+PBMC (MSC to PBMC ratio 1:10) cultures (cultured without any further stimulation for 3 days) using a 2-step magnetic isolation procedure. These cells were irradiated to block any further proliferation and used as stimulators in a mixed lymphocyte reaction (MLR), where responders were allogeneic PBMCs (stimulator to responder ratio 1:100) in the presence of PHA (2.5 μg/ml). The culture was carried out for 48 hours, following which $^3$H thymidine was added. Incorporated radioactivity was counted after 24 hours.

PBMCs were cultured in the absence or presence of MSCs (MSC to PBMC ratio 1:10), following which the non-adherent fraction was harvested and immunostained with FITC-labeled glucocorticoid-induced TNF receptor, or GITR, and PE-labeled CD4.

Generation of $T_H1/T_H2$ Cells

Peripheral blood mononuclear cells (PBMCs) were plated at 2×10$^6$ cells/ml for 45 min. at 37° C. in order to remove monocytes. Non-adherent fraction was incubated in the presence of plate-bound anti-CD3 (5 μg/ml) and anti-CD28 (1 μg/ml) antibodies under $T_H1$ (IL-2 (4 ng/ml)+IL-12 (5 ng/ml)+anti-IL-4 (1 μg/ml)) or $T_H2$ (IL-2 (4 ng/ml)+IL-4 (4 ng/ml)+anti-IFN-γ (1 μg/ml)) conditions for 3 days in the presence or absence of MSCs. The cells were washed and then re-stimulated with PHA (2.5 μg/ml) for another 24 or 48 hours, following which levels of IFN-γ and IL-4 were measured in culture supernatants by ELISA (R&D Systems, Minneapolis, Minn.).

Analysis of Levels of VEGF, PGE$_2$ and Pro-MMP-1 in Culture Supernatant of MSCs.

Using previously characterized human MSCs, the levels of Interleukin-6 (IL-6), VEGF, lipid mediator prostaglandin E$_2$ (PGE$_2$), and matrix metalloproteinase 1 (pro-MMP-1) were analyzed in culture supernatant of MSCs cultured for 24 hours in the presence or absence of PBMCs (MSC to PBMC ratio 1:10).

Proliferation of PBMCs

Purified PBMCs were prepared by centrifuging leukopack (Cambrex, Walkersville, Md.) on Ficoll-Hypaque (Lymphoprep, Oslo, Norway). Separated cells were cultured (in triplicates) in the presence or absence of MSCs (plated 3-4 hours prior to PBMC addition to allow them to settle) for 48 hours in presence of the mitogen PHA (Sigma Chemicals, St. Louis, Mo.). In selected experiments, PBMCs were resuspended in medium containing PGE$_2$ inhibitors Indomethacin (Sigma Chemicals, St. Louis, Mo.) or NS-938 (Cayman Chemicals, Ann Arbor, Mich.). (3H)-thymidine was added (20 μl in a 200 μl culture) and the cells harvested after an additional 24 hour culture using an automatic harvester. The effects of MSCs or PGE$_2$ blockers were calculated as the percentage of the control response (100%) in presence of PHA.

Quantitative RT-PCR

Total RNA from cell pellets were prepared using a commercially available kit (Qiagen, Valencia, Calif.) and according to the manufacturer's instructions. Contaminating genomic DNA was removed using the DNA-free kit (Ambion, Austin, Tex.). Quantitative RT-PCR was performed on a MJ Research Opticon detection system (South San Francisco, Calif.) using QuantiTect SYBR Green RT-PCR kit (Qiagen, Valencia, Calif.) with primers at concentration of 0.5 μM. Relative changes in expression levels in cells cultured under different conditions were calculated by the difference in Ct values (crossing point) using β-actin as internal control. The sequence for COX-1 and COX-2 specific primers were: COX-1: 5'-CCG GAT GCC AGT CAG GAT GAT G-3'(forward) (SEQ ID NO:1), 5'-CTA GAC AGC CAG ATG CTG ACA G-3' (reverse) (SEQ ID NO:2); COX-2: 5'-ATC TAC CCT CCT CAA GTC CC-3' (forward) (SEQ ID NO:3), 5'-TAC CAG AAG GGC AGG ATA CAG-3' (reverse) (SEQ ID NO:4).

Increasing numbers of allogeneic PBMCs were incubated with constant numbers of MSCs (2,000 cells/well) plated on a 96-well plate in the presence of PHA (2.5 μg/ml) for 72 hours, and $^3$H thymidine incorporation (counts per minute, cpm) was determined. The PBMCs and MSCs were cultured at ratios of MSC:PBMC of 1:1, 1:3, 1:10, 1:30, and 1:81.

Results

In the present studies, the interaction of human MSCs with isolated immune cell populations, including dendritic cells (DC1 and DC2), effector T cells (T$_H$1 and T$_H$2) and NK cells was examined. The interaction of MSCs with each immune cell type had specific consequences, suggesting that MSCs may modulate several steps in the immune response process. The production of secreted factor(s) that modulate and may be responsible for MSC immuno-modulatory effects was evaluated and prostaglandin synthesis was implicated.

Figure 1B:
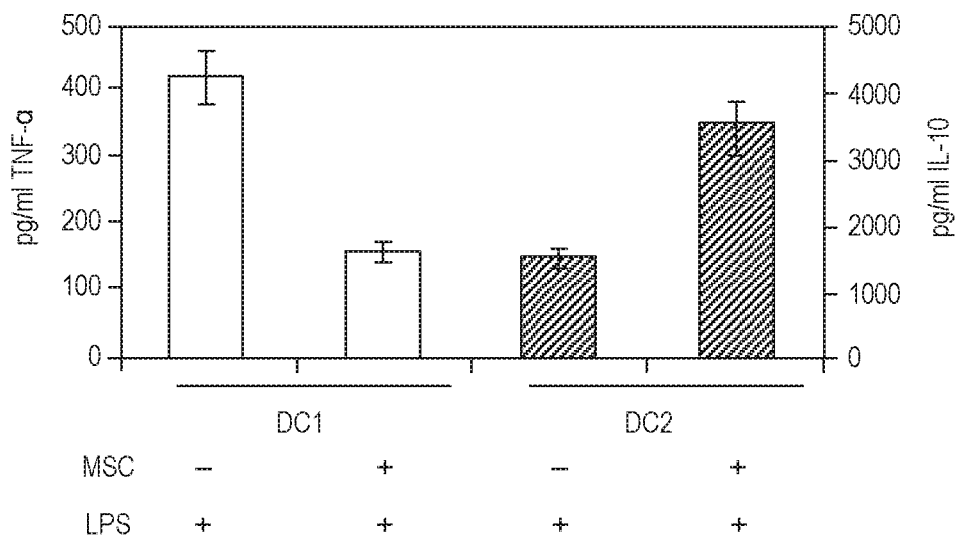
Figure 1C:
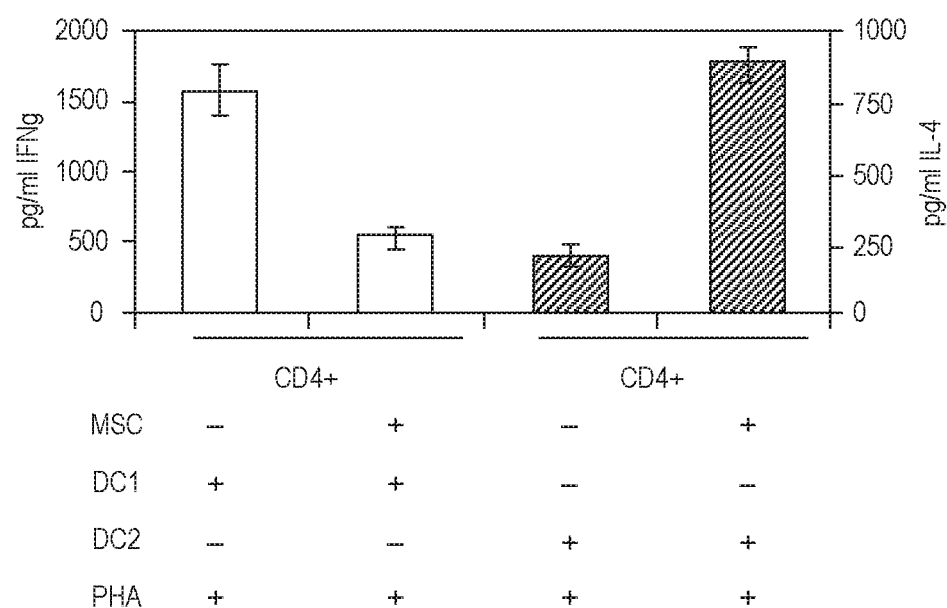

Myeloid (DC1) and plasmacytoid (DC2) precursor dendritic cells were isolated by immuno-magnetic sorting of BDCA1$^+$ and BDCA2$^+$ cells respectively and matured by incubation with GM-CSF and IL-4 (1×10$^3$ IU/ml and 1×10$^3$ IU/ml, respectively) for DC1 cells, or IL-3 (10 ng/ml) for DC2 cells. Using flow cytometry, DC1 cells were HLA-DR$^+$ and CD11c$^+$, whereas DC2 cells were HLA-DR$^+$ and CD123$^+$ (FIG. 1A). In the presence of the inflammatory agent bacterial lipopolysaccharide (LPS, 1 ng/ml), DC1 cells produced moderate levels of TNF-α but when MSCs were present (ratios examined 1:1 and 1:10), there was >50% reduction in TNF-α secretion (FIG. 1B). On the other hand, DC2 cells produced IL-10 in the presence of LPS and its levels were increased greater than 2-fold upon MSC:DC2 co-culture (1:1) (FIG. 1B). Therefore, the MSCs modified the cytokine profile of activated DCs in culture towards a more tolerogenic phenotype. Additionally, activated DCs, when cultured with MSCs, were able to reduce IFN-γ and increase IL-4 levels secreted by naïve CD4$^+$ T cells (FIG. 1C) suggesting a MSC-mediated shift from pro-inflammatory to anti-inflammatory T cell phenotype.

Figure 2A:
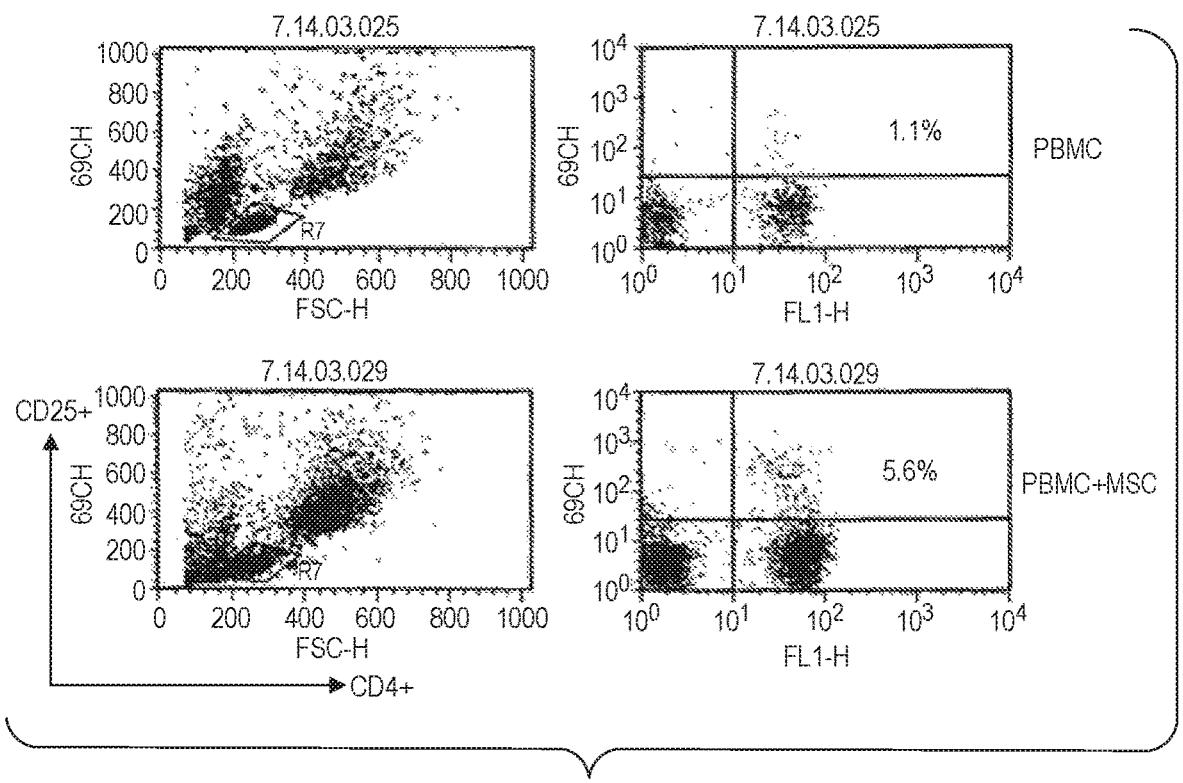
FIGS. 2A-C MSCs inhibit pro-inflammatory effector T cell function. (A) Flow cytometric analysis of $T_{Reg}$ cell numbers (in %) by staining PBMCs or non-adherent fraction in MSC+PBMC culture (MSC+PBMC) with FITC-conjugated CD4 (x-axis) and PE conjugated CD25 (y-axis) antibodies. Gates were set based on isotype control antibodies as background. Graphs are representative of 5 independent experiments. (B) $T_H1$ cells generated in presence of MSCs secreted reduced levels of IFN-γ (primary y-axis) and $T_H2$ cells generated in presence of MSCs secreted increased amounts of IL-4 (secondary y-axis) in cell culture supernatants. (C) MSCs inhibit IFN-γ secretion from purified NK cells cultured for 0, 24, or 48 hours in a 24-well plate. Data shown are mean±SD cytokine secretion in one experiment and are representative of 3 independent experiments.
Figure 2B:
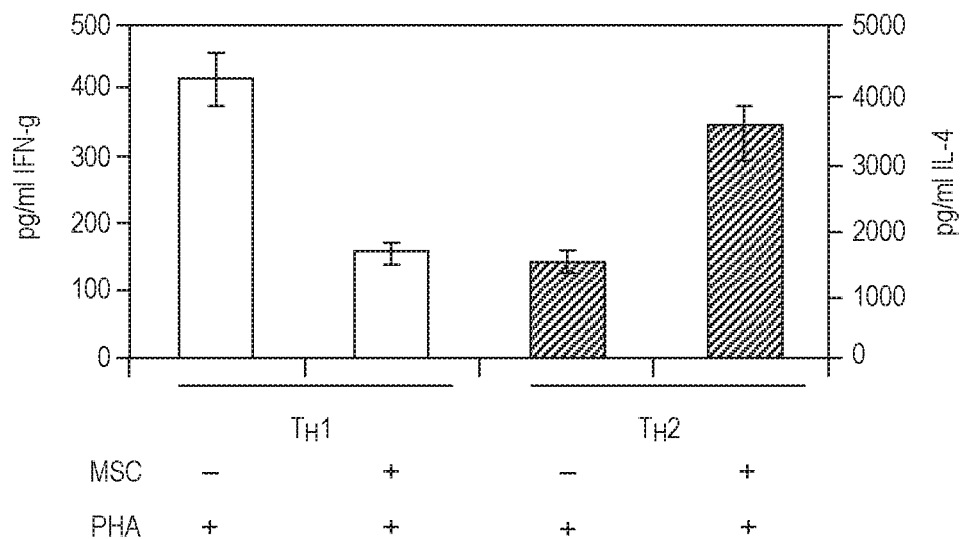
Figure 3A:
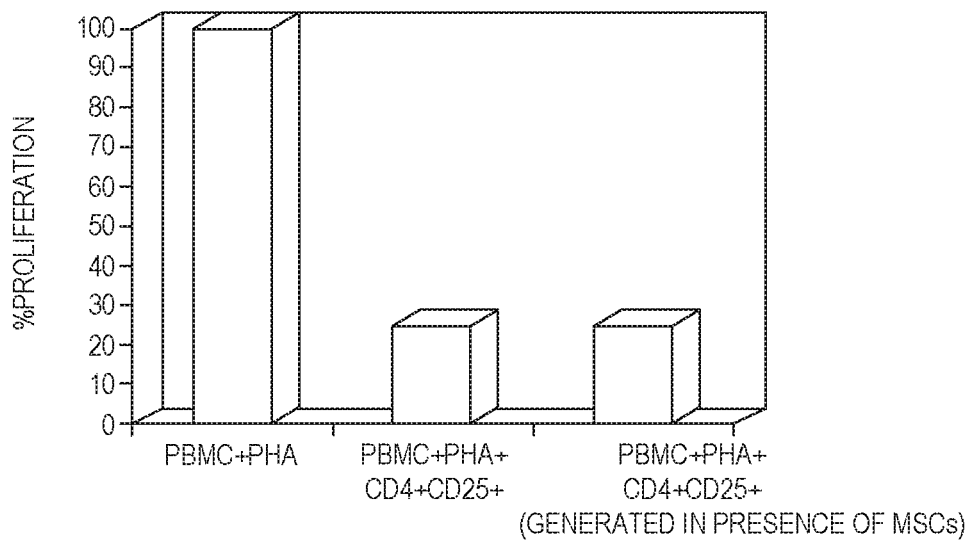
FIGS. 3A-B MSCs lead to increased numbers of $T_{reg}$ cell population and increased GITR expression. (A) A CD4$^+$ CD25$^+$ $T_{reg}$ cell population from PBMC or MSC+PBMC (MSC to PBMC ratio 1:10) cultures (cultured without any further stimulation for 3 days) was isolated using a 2-step magnetic isolation procedure. These cells were irradiated (to block any further proliferation) and used as stimulators in a mixed lymphocyte reaction (MLR), where responders were allogeneic PBMCs (stimulator to responder ratio 1:100) in the presence of phytohemagglutinin (PHA) (2.5 mg/ml). The cells were cultured for 48 hours, following which $^3$H thymidine was added, and incorporated radioactivity was counted after 24 hours. The results showed that the $T_{reg}$ population generated in the presence of MSCs (lane 3) was similar functionally to the $T_{reg}$ cells generated in the absence of MSCs (lane 2). (B) PBMCs were cultured for 3 days in the absence (top plot) or presence (bottom plot) of MSCs (MSC to PBMC ratio 1:10), following which the non-adherent fraction was harvested and immunostained with FITC-labeled GITR and PE-labeled CD4. Results show a greater than twofold increase in GITR expression in cells cultured in the presence of MSCs.
Figure 3B:
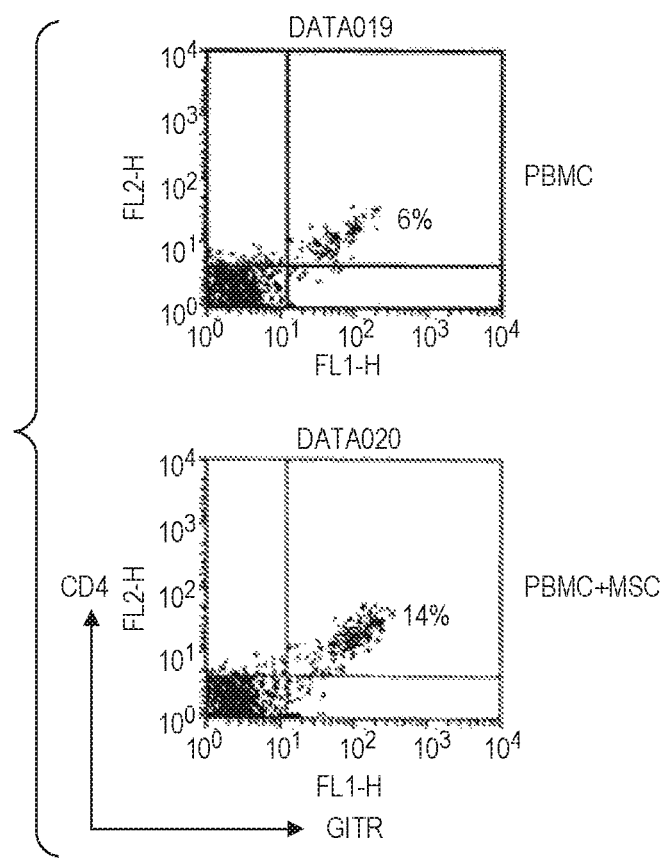

As increased IL-10 secretion plays a role in generation of regulatory cells (Kingsley, et al., *J. Immunol.*, Vol. 168, pg. 1080 (2002)), T-regulatory cells (T$_{Reg}$) were quantified by flow cytometry in co-cultures of PBMCs and MSCs. Upon culture of PBMCs with MSCs for 3-5 days, there was an increase in T$_{Reg}$ cell numbers as determined by staining of PBMCs with anti-CD4 and anti-CD25 antibodies (FIG. 2A), further supporting a MSC-induced tolerogenic response. The CD4$^+$CD25$^+$ T$_{Reg}$ cell population, generated in presence of MSCs expressed increased levels of gluocorticoid-induced TNF receptor (GITR), a cell surface receptor expressed on T$_{Reg}$ cell populations, and was suppressive in nature as it suppressed allogeneic T cell proliferation (FIG. 3A,B). Next, MSCs were investigated as to their direct ability to affect T cell differentiation. Using antibody selected purified T cells (CD4$^+$ Th cells), IFN-γ producing T$_H$1 and IL-4 producing T$_H$2 cells were generated in presence or absence of MSCs. When MSCs were present during differentiation, there was reduced IFN-γ secretion by T$_H$1 cells and increased IL-4 secretion by T$_H$2 cells (FIG. 2B). No significant change in IFN-γ or IL-4 levels were seen when MSCs were added to the culture after Th cells had differentiated (at 3 days) into effector T$_H$1 or T$_H$2 types (data not shown). These experiments suggest that MSCs can affect effector T cell differentiation directly and alter the T cell cytokine secretion towards a humoral phenotype.

Figure 2C:
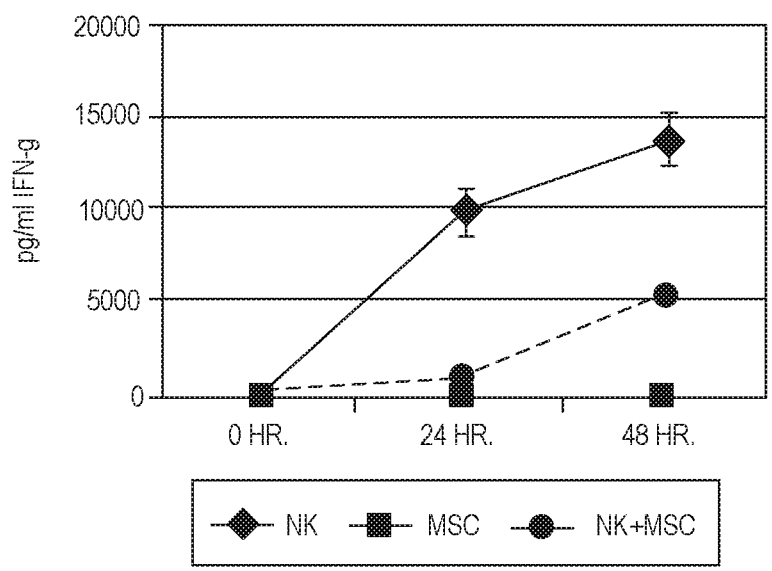

Similarly, when MSCs were cultured with purified NK cells (CD3−, CD14−, CD19−, CD36$^-$) at a ratio 1:1 for different time periods (0-48 hrs), there was decreased IFN-γ secretion in the culture supernatant (FIG. 2C), thereby suggesting that MSCs can modulate NK cell functions also.

Figure 4A:
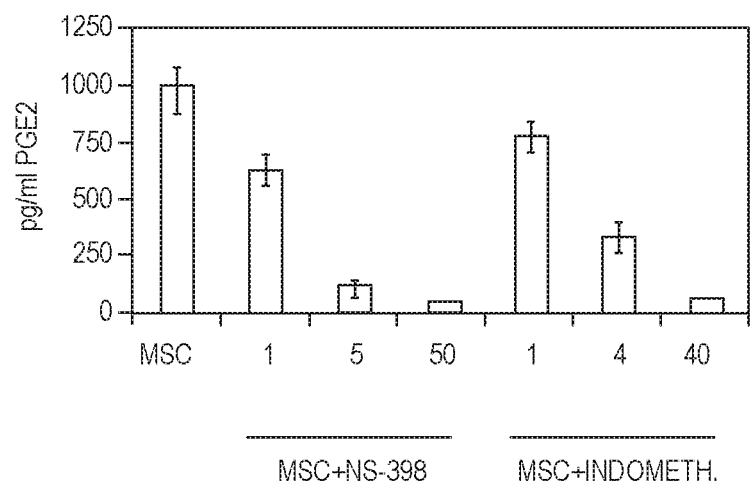
FIGS. 4A-D MSCs produce PGE2 and blocking $PGE_2$ reverses MSC-mediated immune-modulatory effects. (A) $PGE_2$ secretion (mean±SD) in culture supernatants obtained from MSCs cultured in the presence or absence of $PGE_2$ blockers NS-398 or indomethacin (Indometh.) at various concentrations. Inhibitor concentrations are in μM and data presented are values obtained after 24 hour culture (B) COX-1 and COX-2 expression in MSCs and PBMCs using real-time RT-PCR. MSCs expressed significantly higher levels of COX-2 as compared to PBMCs, and when MSCs were cultured in presence of PBMCs, there was a >3-fold increase in COX-2 expression in MSCs. Representative data from 1 of 3 independent experiments is shown. The MSC+ PBMC cultures were setup in a trans-well chamber plate where MSCs were plated onto the bottom chamber and PBMCs onto the top chamber. (C) Presence of $PGE_2$ blockers indomethacin (Ind.) or NS-398 increases TNF-α secretion from activated DCs (□) and IFN-γ secretion from $T_H1$ cells (■) as compared to controls. Data were calculated as % change from cultures generated in absence of MSCs and $PGE_2$ inhibitors (D) Presence of $PGE_2$ blockers indomethacin (Indo) and NS-398 during MSC-PBMC co-culture (1:10) reverses MSC-mediated anti-proliferative effects on PHA-treated PBMCs. Data shown are from one experiment and are representative of 3 independent experiments.
Figure 4B:
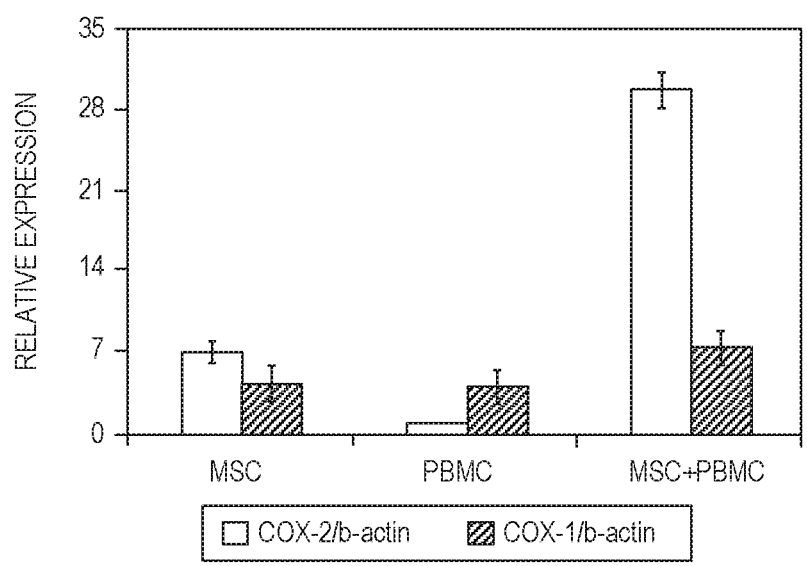
Figure 4C:
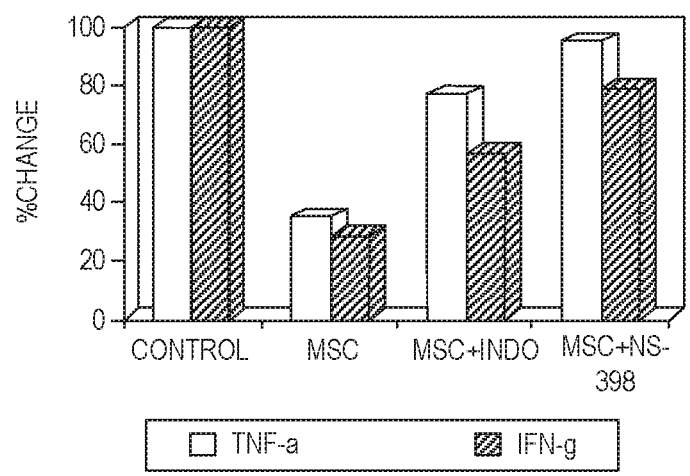
Figure 4D:
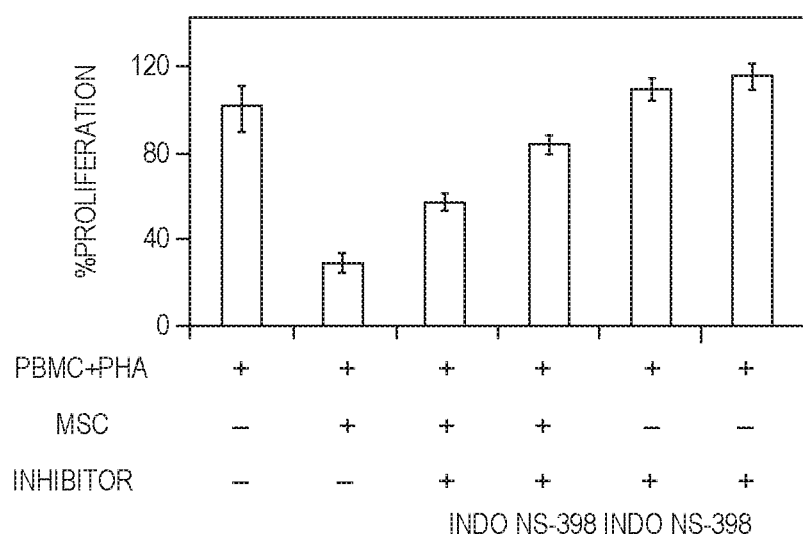
Figure 5:
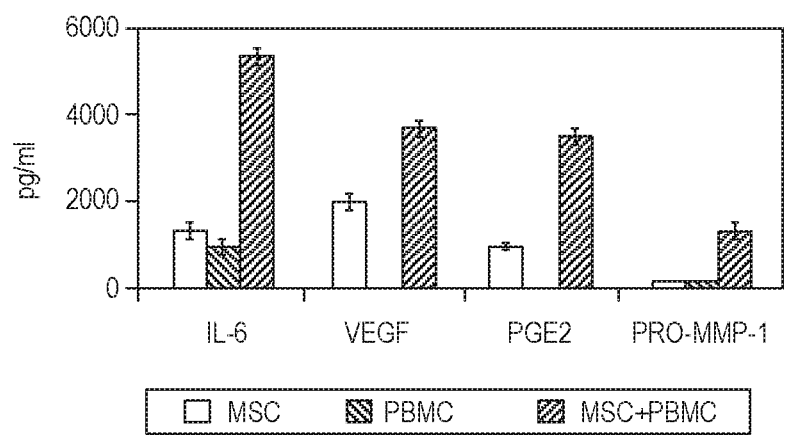
FIG. 5 Constitutive MSC cytokine secretion is elevated in the presence of allogeneic PBMCs. Using previously characterized human MSCs, the levels of the cytokines IL-6 and VEGF, lipid mediator $PGE_2$, and matrix metalloproteinase 1 (pro-MMP-1) in culture supernatant of MSCs cultured for 24 hours in the presence (hatched bars) or absence (open bars) of PBMCs (MSC to PBMC ratio 1:10) were analyzed. The MSCs produced IL-6, VEGF, and $PGE_2$ constituitively, and the levels of these factors increased upon co-culture with PBMCs, thereby suggesting that MSCs may play a role in modulating immune functions in an inflammatory setting.
Figure 6:
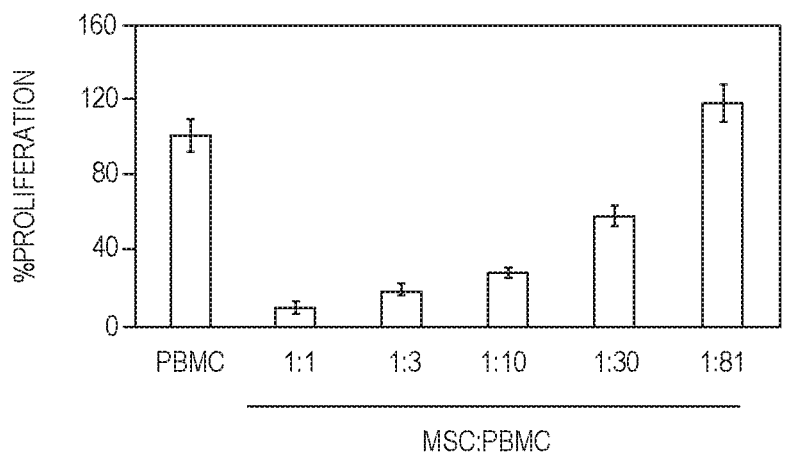
FIG. 6 MSCs inhibit mitogen-induced T-cell proliferation in a dose-dependent manner. Increasing numbers of allogeneic PBMCs were incubated with constant numbers of MSCs (2,000 cells/well) plated on a 96-well plate in the presence or absence of PHA (2.5 mg/ml) for 72 hours, and $^3$H thymidine incorporation determined (in counts per minute, or cpm). There was a dose-dependent inhibition of the proliferation of PHA-treated PBMCs in the presence of MSCs. Representative results from 1 of 3 independent experiments are shown. Similar results were reported by LeBlanc, et al., *Scand J. Immunol.*, Vol. 57, pg. 11 (2003).

Previous work has indicated that MSCs modify T-cell functions by soluble factor(s) (LeBlanc, et al., *Exp. Hematol.*, Vol. 31, pg. 890 (2003); Tse, et al., *Transplantation*, Vol. 75, pg. 389 (2003)). It was observed that the MSCs secreted several factors, including IL-6, prostaglandin E$_2$, VEGF and proMMP-1 constitutively, and the levels of each increased upon culture with PBMCs (FIG. 5). In order to investigate MSC-derived factors leading to inhibition of TNF-α and increase of IL-10 production by DCs, the potential role of prostaglandin E$_2$ was investigated, as it has been shown to inhibit TNF-α production by activated DCs (Vassiliou, et al., *Cell. Immunol.*, Vol. 223, pg. 120 (2003)). Conditioned media from MSC culture (24 hour culture of 0.5×10$^6$ cells/ml) contained approx. 1000 μg/ml of PGE$_2$ (FIG. 4A). There was no detectable presence of known inducers of PGE$_2$ secretion, e.g., TNF-α, IFN-γ or IL-1β (data not shown) in the culture supernatant indicating a constitutive secretion of PGE$_2$ by MSCs. The PGE$_2$ secretion by hMSCs was inhibited 60-90% in the presence of known inhibitors of PGE$_2$ production, NS-398 (5 pM) and indomethacin (4 pM) (FIG. 4A). As the release of PGE$_2$ secretion occurs as a result of enzymatic activity of constitutively active cycloxygenase enzyme 1 (COX-1) and inducible cycloxygenase enzyme 2 (COX-2) (Harris, et al., *Trends Immunol.*, Vol. 23, pg. 144 (2002)) the mRNA expression for COX-1 and COX-2 in MSCs and PBMCs using trans-well culture system was analyzed. MSCs expressed significantly higher levels of COX-2 as compared to PBMCs and the expression levels increase >3-fold upon co-culture of MSCs and PBMCs (MSC to PBMC ratio 1:10) for 24 hours (FIG. 4B). Modest changes in COX-1 levels were seen suggesting that the increase in PGE$_2$ secretion upon MSC-PBMC co-culture (FIG. 5) is mediated by COX-2 up-regulation. To investigate whether the immunomodulatory effects of MSC on DCs and T-cells were mediated by PGE$_2$, MSCs were cultured with activated dendritic cells (DC1) or T$_H$1 cells in the presence of PGE$_2$ inhibitors NS-398 or indomethacin. The presence of NS-398 or indomethacin increased TNF-α secretion by DC1s, and IFN-γ secretion from T$_H$1 cells (FIG. 4C), respectively, suggesting that MSC effects on immune cell types may be mediated by secreted PGE$_2$. Recent studies have shown that MSCs inhibit T-cell proliferation induced by various stimuli (DeNicola, et al., *Blood*, Vol. 99, pg. 3838 (2002); LeBlanc, et al., *Scand. J. Immunol.*, Vol. 57, pg. 11 (2003)). It was observed that MSCs inhibit mitogen-induced T cell proliferation in a dose-dependent manner (FIG. 6) and when PGE$_2$ inhibitors NS-398 (5 pM) or indomethacin (4 pM) were present, there was a >70% increase in ($^3$H) thymidine incorporation by PHA-treated PBMCs in MSC containing cultures as compared to controls without inhibitors (FIG. 4D).

Figure 7:
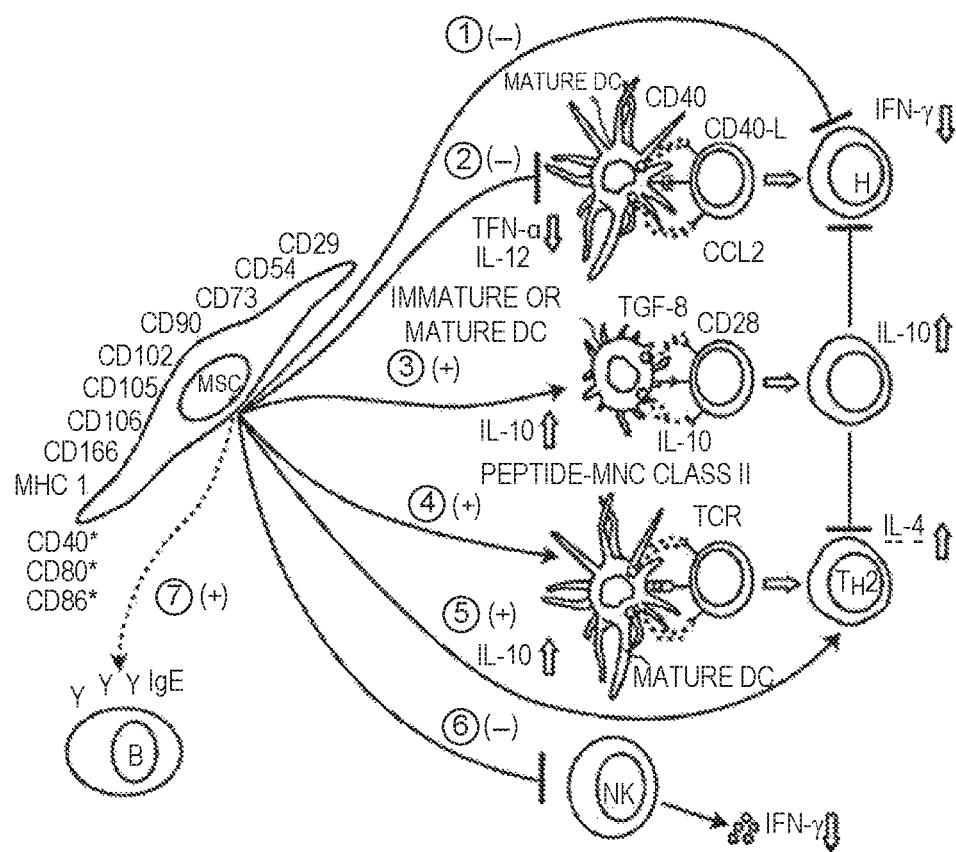
FIG. 7 Schematic diagram of proposed MSC mechanism of action. MSCs mediate their immuno-modulatory effects by affecting cells from both the innate (DCs-pathways 2-4; and NK-pathway 6) and adaptive (T-pathways 1 and 5 and B-pathway 7) immune systems. In response to an invading pathogen, immature DCs migrate to the site of potential entry, mature and acquire an ability to prime naïve T cells (by means of antigen specific and co-stimulatory signals) to become protective effector T cells (cell-mediated $T_H1$ or humoral $T_H2$ immunity). During MSC-DC interaction, MSCs, by means of direct cell-cell contact or via secreted factor, may alter the outcome of immune response by limiting the ability of DCs to mount a cell-mediated response (pathway 2) or by promoting the ability to mount a humoral response (pathway 4). Also, when mature effector T cells are present, MSCs may interact with them to skew the balance of $T_H1$ (pathway 1) responses towards $T_H2$ responses (pathway 5), and probably towards an increased IgE producing B cell activity (pathway 7), desirable outcomes for suppression of GvHD and autoimmune disease symptoms. MSCs in their ability to result in an increased generation of $T_{Reg}$ population (pathway 3) may result in a tolerant phenotype and may aid a recipient host by dampening bystander inflammation in their local micro-environment. Dashed line (----) represents proposed mechanism.

In summary, a model of MSC interaction with other immune cell types (FIG. 7) is proposed. When mature T cells are present, MSCs may interact with them directly and inhibit the pro-inflammatory IFN-γ production (pathway 1) and promote regulatory T cell phenotype (pathway 3) and anti-inflammatory T$_H$2 cells (pathway 5). Further, MSCs can alter the outcome of the T cell immune response through DCs by secreting PGE$_2$, inhibiting pro-inflammatory DC1 cells (pathway 2) and promoting anti-inflammatory DC2 cells (pathway 4) or regulatory DCs (pathway 3). A shift towards T$_H$2 immunity in turn, suggests a change in B cell activity towards increased generation of IgE/IgG1 subtype antibodies (pathway 7). MSCs, by their ability to inhibit IFN-γ secretion from NK cells likely modify NK cell function (pathway 6). This model of MSC: Immune cell interactions is consistent with the experimentation performed in several other laboratories (LeBlanc, et al., *Exp. Hematol.*, Vol. 31, pg. 890 (2003); Tse, et al., *Transplantation*, Vol. 75, pg. 389 (2003); DiNicola, et al., *Blood*, Vol. 99, pg. 3838 (2002)). Further examination of the proposed mechanisms is underway and animal studies are now necessary to examine the in vivo effects of MSC administration.

Example 2

Mesenchymal stem cells were given to a 33-year-old female patient suffering from severe Grade IV gastrointestinal graft-versus-host disease (GVHD). The patient was refractory to all other GVHD treatments. Endoscopic views of the patient's colon showed areas of ulceration and inflammation prior to treatment. Histology of the patient's colon showed that the graft-versus-host disease had destroyed the vast majority of the patient's intestinal crypts, prior to treatment.

The patient was given an intravenous infusion of allogeneic mesenchymal stem cells in 50 ml of Plasma Lyte A in an amount of 3×10$^6$ cells per kilogram of body weight.

The patient was evaluated at two weeks post-infusion. At two weeks post-infusion, an endoscopic view of the patient's colon showed that the areas of inflammation and ulceration visible prior to treatment were resolved. In addition, a biopsy of the patient's colon showed significant regeneration of intestinal crypts. Thus, the administration of the mesenchymal stem cells to the patient resulted in a significant reduction in the inflammatory component of gastrointestinal graft-versus-host disease, and resulted in the regeneration of new functional intestinal tissue.

The disclosures of all patents, publications, including published patent applications, depository accession numbers, and database accession numbers are hereby incorporated by reference to the same extent as if each patent, publication, depository accession number, and database accession number were specifically and individually incorporated by reference.

It is to be understood, however, that the scope of the present invention is not to be limited to the specific embodiments described above. The invention may be practiced other than as particularly described and still be within the scope of the accompanying claims.

The invention claimed is:

1. A method of treating an inflamed wound in a human in need thereof comprising administering isolated mesenchymal stem cells to the human in an amount effective to treat the inflamed wound, wherein the mesenchymal stem cells are genetically unmanipulated.

2. The method of claim 1, wherein the wound is internal or external.

3. The method of claim 1, wherein the wound is a dermal ulcer.

4. The method of claim 3, wherein the dermal ulcer is caused by diabetes or sickle cell-anemia.

5. The method of claim 1, wherein the mesenchymal stem cells are administered directly into the wound.

6. The method of claim 1, wherein the mesenchymal stem cells are administered as a cell suspension in a pharmaceutically acceptable liquid medium or on a dressing or reservoir.

7. The method of claim 1, wherein the mesenchymal stem cells are allogeneic.

8. The method of claim 2, wherein the mesenchymal stem cells are allogeneic.

9. The method of claim 6, wherein the mesenchymal stem cells are allogeneic.

10. The method of claim 1, wherein the mesenchymal stem cells are autologous.

11. The method of claim 2, wherein the mesenchymal stem cells are autologous.

12. The method of claim 6, wherein the mesenchymal stem cells are autologous.

13. The method of claim 1, wherein the mesenchymal stem cells are harvested from a mesenchymal stem cell-containing tissue, isolated, and expanded in culture.

14. The method of claim 2, wherein the mesenchymal stem cells are harvested from a mesenchymal stem cell-containing tissue, isolated, and expanded in culture.

15. The method of claim 6, wherein the mesenchymal stem cells are harvested from a mesenchymal stem cell-containing tissue, isolated, and expanded in culture.

16. The method of claim 9, wherein the mesenchymal stem cells are harvested from a mesenchymal stem cell-containing tissue, isolated, and expanded in culture.

17. The method of claim 13, wherein the mesenchymal stem cell-containing tissue is blood, skin, cord blood, muscle, fat, perichondrium, bone marrow or periosteum.

18. The method of claim 14, wherein the mesenchymal stem cell-containing tissue is blood, skin, cord blood, muscle, fat, perichondrium, bone marrow or periosteum.

19. The method of claim 15, wherein the mesenchymal stem cell-containing tissue is blood, skin, cord blood, muscle, fat, perichondrium, bone marrow or periosteum.

20. The method of claim 16, wherein the mesenchymal stem cell-containing tissue is blood, skin, cord blood, muscle, fat, perichondrium, bone marrow or periosteum.

21. The method of claim 1, wherein the mesenchymal stem cells are administered in combination with an anti-inflammatory drug.

22. The method of claim 1, wherein the mesenchymal stem cells promote angiogenesis.

23. The method of claim 1, wherein the mesenchymal stem cells promote release of IL-10.

* * * * *